(12) United States Patent
Lee et al.

(10) Patent No.: US 10,967,094 B2
(45) Date of Patent: *Apr. 6, 2021

(54) PURIFIED HYDROGEN PEROXIDE GAS GENERATION METHODS AND DEVICES

(71) Applicant: Synexis LLC, Kansas City, MO (US)

(72) Inventors: James D. Lee, Kansas City, MO (US); Douglas J. Bosma, Kansas City, MO (US)

(73) Assignee: Synexis LLC, Overland Park, KS (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/271,331

(22) Filed: Feb. 8, 2019

(65) Prior Publication Data

US 2019/0167832 A1 Jun. 6, 2019

Related U.S. Application Data

(63) Continuation of application No. 15/308,771, filed as application No. PCT/US2015/029276 on May 5, 2015, now Pat. No. 10,232,076.

(Continued)

(51) Int. Cl.
*A61L 9/00* (2006.01)
*A61N 5/00* (2006.01)
(Continued)

(52) U.S. Cl.
CPC .......... *A61L 9/14* (2013.01); *A61L 9/16* (2013.01); *B01J 21/063* (2013.01); *B01J 23/30* (2013.01); *B01J 35/004* (2013.01); *B01J 35/06* (2013.01); *B01J 37/0225* (2013.01); *C01B 15/027* (2013.01); *F24F 3/1411* (2013.01); *F24F 3/16* (2013.01); *A61L 2209/12* (2013.01); *A61L 2209/14* (2013.01); *A61L 2209/16* (2013.01);
(Continued)

(58) Field of Classification Search
CPC ...... A62B 7/08; A61M 16/01; C01B 13/0207; A61L 9/12; A61L 2/208; A61L 9/20
USPC ................. 422/24, 305; 250/492.1
See application file for complete search history.

(56) References Cited

U.S. PATENT DOCUMENTS 3,454,385 A * 7/1969 Amero ................ C09K 3/1418
51/298
8,168,122 B2 5/2012 Lee
(Continued)

FOREIGN PATENT DOCUMENTS

CN 102 021 676 A 4/2011
EP 0 826 531 A2 3/1998
(Continued)

OTHER PUBLICATIONS

Anonymous, "Development of a High-performance Photocatalyst that is Surface-treated with Cesium," dated May 17, 2010, available on the internet at http://www.aist.go.jp/aist_e/list/latest_research/2010/20100517/20100517.html.

(Continued)

Primary Examiner — Monzer R Chorbaji
(74) Attorney, Agent, or Firm — Arnold & Porter Kaye Scholer

(57) ABSTRACT

The present disclosure provides for and includes improved devices and methods for the production of Purified Hydrogen Peroxide Gas (PHPG) that is substantially non-hydrated and substantially free of ozone.

11 Claims, 6 Drawing Sheets

Related U.S. Application Data

(60) Provisional application No. 61/988,535, filed on May 5, 2014.

(51) Int. Cl.

| | | |
|---|---|---|
| *A61L 9/14* | (2006.01) | |
| *C01B 15/027* | (2006.01) | |
| *B01J 37/02* | (2006.01) | |
| *B01J 23/30* | (2006.01) | |
| *B01J 35/00* | (2006.01) | |
| *B01J 21/06* | (2006.01) | |
| *B01J 35/06* | (2006.01) | |
| *A61L 9/16* | (2006.01) | |
| *F24F 3/14* | (2006.01) | |
| *F24F 3/16* | (2021.01) | |

(52) U.S. Cl.
CPC . *A61L 2209/211* (2013.01); *F24F 2003/1628* (2013.01); *F24F 2003/1667* (2013.01)

(56) References Cited

U.S. PATENT DOCUMENTS

| | | | |
|---|---|---|---|
| 8,658,101 B1 | 2/2014 | Burnett | |
| 8,684,329 B2 | 4/2014 | Song et al. | |
| 9,034,255 B2 | 5/2015 | Lee | |
| 10,232,076 B2* | 3/2019 | Lee | F24F 3/16 |
| 2004/0224147 A1 | 11/2004 | Chou | |
| 2005/0191205 A1 | 9/2005 | Uslenghi et al. | |
| 2009/0010801 A1 | 1/2009 | Murphy et al. | |
| 2009/0041617 A1* | 2/2009 | Lee | A61L 9/205 422/4 |
| 2009/0211453 A1* | 8/2009 | Nassivera | B01D 53/58 96/153 |
| 2010/0116138 A1* | 5/2010 | Guimond | B01D 39/1615 96/11 |
| 2011/0182773 A1 | 7/2011 | Holt | |

FOREIGN PATENT DOCUMENTS

| | | |
|---|---|---|
| EP | 0 893 128 A2 | 1/1999 |
| JP | H11-276906 A | 10/1999 |
| JP | 2006-296811 | 11/2006 |
| JP | 2011-56155 | 3/2011 |
| JP | 2012-517862 | 8/2012 |
| WO | WO 2010/093796 A1 | 8/2010 |
| WO | WO 2011/016206 A1 | 2/2011 |
| WO | WO 2012/153272 A1 | 11/2012 |
| WO | WO 2015/026958 A1 | 2/2015 |

OTHER PUBLICATIONS

Blake et al., "Application of the Photocatalytic Chemistry of Titanium Dioxide to Disinfection and the Killing of Cancer Cells," *Separation and Purification Methods*, 28(1):1-50 (1999).
International Search Report issued in Application No. PCT/US2015/029276 dated Jul. 31, 2015.
Search Report dated Dec. 13, 2018, in Russian Patent Application No. 2016145927.
Shon et al., "Visible Light Responsive Titanium Dioxide ($TiO_2$)—a review," available at epress.lib.uts.edu.au (2008).
Sugihara et al., "Development of a Visible Light Responsive Photocatalyst using Tungsten Oxide under Indoor Lighting," National Institute of Advance Industrial Science and Technology (AIST) (2008).
Tükenmez, "Tungsten Oxide Nanopowders and Its Photocatalytic Activity under Visible Light Irradiation," Thesis, Department of Molecular Biology, Umea University, Sweden (2013).
Extended European Search Report dated May 3, 2019, in European Patent Application No. 19159041.3.
Khataee et al., "Photocatalytic decolorization and mineralization of orange dyes on immobilized titanium dioxide nanoparticles," *Water Science & Technology*, 62(5):1112-1120 (2010).
Ko et al., "High performance nano-titania photocatalytic paper composite. Part II: Preparation and characterization of natural zeolite-based nano-titania composite sheets and study of their photocatalytic activity," *Materials Science and Engineering B*, 164:135-139 (2009).
Merajin et al., "Photocatalytic conversion of greenhouse gases ($CO_2$ and $CH_4$) to high value products using $TiO_2$ nanoparticles supported on stainless steel webnet," *Journal of the Taiwan Institute of Chemical Engineers*, 44:239-246 (2013).
Ochiai et al., "Photocatalytic inactivation and removal of algae with $TiO_2$-coated materials," *J Appl Electrochem*, 40:1737-1742 (2010).
Written Opinion dated Feb. 25, 2020, in Singaporean Patent Application No. 10201805181U (7 pgs.)

* cited by examiner

PURIFIED HYDROGEN PEROXIDE GAS GENERATION METHODS AND DEVICES

RELATED APPLICATIONS

This application is a continuation of U.S. patent application Ser. No. 15/308,771, filed Nov. 3, 2016, which is a national stage application of International Application No. PCT/US2015/029276 filed May 5, 2015, which claims priority to U.S. Provisional Application No. 61/988,535, filed May 5, 2014, each of which is hereby incorporated by reference in their entireties.

FIELD

The present disclosure relates generally to improved methods and devices for the production of purified hydrogen peroxide gas (PHPG). More specifically, this disclosure relates to improved air permeable surfaces, catalytic surfaces and methods for increased production of PHPG.

BACKGROUND

Pathogenic microbes, molds, mildew, spores, and organic and inorganic pollutants are commonly found in the environment. Microbial control and disinfection in environmental spaces is desirable to improve health. Numerous ways have been used in the past in an attempt to purify air and disinfect surfaces. For example, it is already known that Reactive Oxygen Species (ROS) produced by, e.g., photocatalytic oxidation process can oxidize organic pollutants and kill microorganisms. More particularly, hydroxyl radical, hydroperoxyl radicals, chlorine and ozone, end products of the photocatalytic reaction, have been known to be capable of oxidizing organic compounds and killing microorganisms. However, there are limitations to the known methods and devices, not only due to efficacy limitation but also due to safety issues.

ROS is the term used to describe the highly activated air that results from exposure of ambient humid air to ultraviolet light. Light in the ultraviolet range emits photons at a frequency that when absorbed has sufficient energy to break chemical bonds. UV light at wavelengths of 250-255 nm is routinely used as a biocide. Light below about 181 nm, up to 182-187 nm is competitive with corona discharge in its ability to produce ozone. Ozonation and UV radiation are both being used for disinfection in community water systems. Ozone is currently being used to treat industrial wastewater and cooling towers.

Hydrogen peroxide is generally known to have antimicrobial properties and has been used in aqueous solution for disinfection and microbial control. Attempts to use hydrogen peroxide in the gas phase however, have previously been hampered by technical hurdles to the production of Purified Hydrogen Peroxide Gas (PHPG). Vaporized aqueous solutions of hydrogen peroxide produce an aerosol of microdroplets composed of aqueous hydrogen peroxide solution. Various processes for "drying" vaporized hydrogen peroxide (VHP) solutions produce, at best, a hydrated form of hydrogen peroxide. These hydrated hydrogen peroxide molecules are surrounded by water molecules bonded by electrostatic attraction and London Forces. Thus, the ability of the hydrogen peroxide molecules to directly interact with the environment by electrostatic means is greatly attenuated by the bonded molecular water, which effectively alters the fundamental electrostatic configuration of the encapsulated hydrogen peroxide molecule. Further, the lowest concentration of vaporized hydrogen peroxide that can be achieved is generally well above the 1.0 ppm Occupational Safety and Health Administration (OSHA) workplace safety limit, making these processes unsuitable for use in occupied areas.

Photocatalysts that have been demonstrated for the destruction of organic pollutants in fluid include but are not limited to $TiO_2$, ZnO, $SnO_2$, $WO_3$, CdS, $ZrO_2$, $SB_2O_4$, and $Fe_2O_3$. Titanium dioxide is chemically stable, has a suitable bandgap for UV/Visible photoactivation, and is relatively inexpensive. Therefore, photocatalytic chemistry of titanium dioxide has been extensively studied over the last thirty years for removal of organic and inorganic compounds from contaminated air and water.

Because photocatalysts can generate hydroxyl radicals from adsorbed water when activated by ultraviolet light of sufficient energy, they show promise for use in the production of PHPG for release into the environment when applied in the gas phase. Existing applications of photocatalysis, however, have focused on the generation of a plasma containing many different reactive chemical species. Further, the majority of the chemical species in the photocatalytic plasma are reactive with hydrogen peroxide, and inhibit the production of hydrogen peroxide gas by means of reactions that destroy hydrogen peroxide. Also, any organic gases that are introduced into the plasma inhibit hydrogen peroxide production both by direct reaction with hydrogen peroxide and by the reaction of their oxidized products with hydrogen peroxide.

The photocatalytic reactor itself also limits the production of PHPG for release into the environment. Because hydrogen peroxide has greater chemical potential than oxygen to be reduced as a sacrificial oxidant, it is preferentially reduced as it moves downstream in photocatalytic reactors as rapidly as it is produced by the oxidation of water.

TABLE 1

| Oxidation/Reduction Half Reactions | |
|---|---|
| Photo-Activation of Catalyst | Standard Reduction Potential (eV) |
| $hv \leftrightarrows h^+ + e^-$ (on $TiO_2$ catalyst) | ≤−3.2 |
| $hv \leftrightarrows h^+ + e^-$ (on $TiO_2$ catalyst with co-catalyst) | ≤−2.85 |
| Loss of Free Electrons Due to Electron-Hole Recombination | |
| $h^+ + e^- \leftrightarrows$ heat (on $TiO_2$ catalyst) | ≥3.2 |
| $h^+ + e^- \leftrightarrows$ heat (on $TiO_2$ catalyst with co-catalyst) | ≥2.85 |
| Formation of Hydroxyl Radicals (only if water is adsorbed on active sites on catalyst, preventing Electron-Hole Recombination) | |
| $h^+ + H_2O \leftrightarrows OH^* + H^+$ | 2.85 |
| Thermodynamically Favored loss of Hydroxyl Radicals by Free Electron Reduction in a Concentrated Plasma Reactor, but Avoided in a PHPG Reactor | |
| $OH^* + e^- + H^+ \leftrightarrows H_2O$ | 2.02 |
| Combination of Hydroxyl Radicals to Form Hydrogen Peroxide is not Thermodynamically Favored Compared to Free Electron Reduction in a Plasma Reactor, but is Promoted by a PHPG Reactor by Creating a Dilute Hydroxyl Radical Field Separated from Free Electrons | |
| $2OH^* \leftrightarrows H_2O_2$ | 1.77 |
| Spontaneous Reactions That would Destroy any Hydrogen Peroxide in Concentrated Plasma Reactors, but which are Avoided by a PHPG Reactor by Creating a Dilute Hydroxyl Radical | |

TABLE 1-continued Oxidation/Reduction Half Reactions

| Photo-Activation of Catalyst | Standard Reduction Potential (eV) |
|---|---|
| Field Separated from Free Electrons and Light | |
| $2OH^* + H_2O_2 \leftrightarrows 2H_2O + O_2$ | 2.805 |
| $H_2O_2 + 2H^+ + 2e^- \leftrightarrows 2H_2O$ | 1.78 |
| $H_2O_2 + h\nu \leftrightarrows 2OH^*$ (by Photolysis) | 1.77 |
| $e^- + H_2O_2 \leftrightarrows OH^* + OH^-$ | 0.71 |
| Reactions that Create Hydrogen Peroxide through the Forced Reduction of Dioxygen in a PHPG Reactor, but not in a Concentrated Plasma Reactor | |
| $e^- + O_2 \leftrightarrows O_2^-$ (First Step is non-Spontaneous) | −0.13 |
| $2H^+ + 2e^- + O_2 \leftrightarrows H_2O_2$ (Overall Reaction) | 0.70 |
| Other Reactions Common in a Concentrated Plasma Reactor, but which do not take place in a PHPG Reactor, which does not use Ozone-Producing Wavelengths of Light | |
| $O_2 + h\nu \leftrightarrows 2O^*$ (by Photolysis) | ≤−5.13 |
| $2O^* + 2O_2 \leftrightarrows 2O_3$ | 2.99 |
| $O_3 + 2H^+ + 2e^- \leftrightarrows O_{2(g)} + H_2O$ | 2.075 |
| $O_3 + H_2O + 2e^- \leftrightarrows O_{2(g)} + 2OH^-$ | 1.24 |
| Ozone Destruction of Hydrogen Peroxide | |
| $O_3 + H_2O_2 \leftrightarrows H_2O + 2O_2$ | 1.381 |

Additionally, several side reactions generate a variety of species that become part of the photocatalytic plasma, and which inhibit the production of PHPG for release into the environment as noted above.

In general, hydroxyl radicals are produced by the oxidation of water and require an oxidation potential of at least 2.85 eV to take place. The catalyst, therefore, must be activated by photons with at least this required energy. Photons with lower energy than 2.85 eV will not produce hydroxyl radicals, but photons with energy of at least 1.71 eV can photolyse hydrogen peroxide into hydroxyl radicals. Excess light with energy of 1.71 eV or above should be avoided due to the destruction of hydrogen peroxide.

Inside a plasma reactor, where it is possible for free electrons to recombine with hydroxyl radicals and form hydroxide ions, this is the thermodynamically favored reaction because it has the highest reduction potential, 2.02 eV. All reactions with lower reduction potentials, such as the combination of hydroxyl radicals to form hydrogen peroxide, 1.77 eV, are not favored. In rare instances where the formation of hydrogen peroxide occurs, a stoichiometric excess of two free electrons will be created. In this case the stoichiometric excess of free electrons makes it possible for lower potential reactions to take place, most notably the reduction of the hydrogen peroxide molecule into a hydroxyl radical and a hydroxide ion, 0.71 eV, then further down to water by separate reduction of the radical and of the ion.

In a plasma reactor, the abundance of free electrons ensures that the reduction of hydroxyl radicals dominates, and that any hydrogen peroxide that may theoretically be formed is immediately reduced back into water.

In contrast, in a PHPG reactor, production of hydrogen peroxide is favored because the reactor separates hydroxyl radicals from the free electrons, preventing the reduction of the hydroxyl radicals to water. This permits the next most favored reaction to take place, the combination of hydroxyl radicals to form hydrogen peroxide. The hydrogen peroxide can be reduced back down to water by decomposition (reaction of hydrogen peroxide molecules with each other), but this effect is minimized by ensuring that the hydrogen peroxide produced is dilute.

Also, since the PHPG reactor separates hydroxyl radicals from the free electron remaining on the catalyst, the free electrons are forced to reduce another species, in this case dioxygen. The reduction of dioxygen to the superoxide ion has a negative reduction potential, −0.13 eV, which indicates that it is non-spontaneous, but only slightly so. The non-spontaneity is overcome by the build-up of free electrons on the catalyst, creating an increasing thermodynamic reduction pressure. This non-spontaneous reaction is the first of four steps in the reduction of oxygen to hydrogen peroxide, the remaining three of which are all spontaneous. It is important to note that when all four of these steps are combined into a single reduction reaction, the overall potential is positive, or spontaneous. It is easy to overlook the fact that the non-spontaneous first step must take place in order for the three remaining spontaneous steps to follow.

The reduction of dioxygen to hydrogen peroxide, forced by the removal of hydroxyl radicals from the free electrons remaining on the catalyst, results in the desired production of yet more hydrogen peroxide, of course.

The reactions listed in Table 1 are the most pertinent. Other reactions, known in the art can be added and their relative contributions reactions on the catalyst surface determined by their relative potentials compared to the key reactions. Notably, as in the formation of ozone by plasma reactors, another high potential reaction is introduced that destroys hydrogen peroxide. To completely avoid ozone production, one need only avoid the use of light at wavelengths of 186 nm and below.

The wavelengths of light used to activate photocatalysts are also energetic enough to photolyse the peroxide bond in a hydrogen peroxide molecule and are also an inhibitor in the production of PHPG for release into the environment. Further, the practice of using wavelengths of light that produce ozone introduces yet another species into the photocatalytic plasma that destroys hydrogen peroxide.

$$O_3 + H_2O_2 \leftrightarrows H_2O \text{ to } 2O_2$$

In practice, photocatalytic applications have focused on the production of a plasma, often containing ozone, used to oxidize organic contaminants and microbes. Such plasmas are primarily effective within the confines of the reactor itself, by nature have limited chemical stability beyond the confines of the reactor, and actively degrade the limited amounts of hydrogen peroxide gas that they may contain. Further, because the plasma is primarily effective within the reactor itself, many designs maximize residence time to facilitate more complete oxidation of organic contaminants and microbes as they pass through the reactor. Since hydrogen peroxide has such a high potential to be reduced, the maximized residence time results in minimized hydrogen peroxide output.

Also, most applications of photocatalysis produce environmentally objectionable chemical species. First among these is ozone itself, an intentional product of many systems. Further, since organic contaminants that pass through a reactor are seldom oxidized in one exposure, multiple air exchanges are necessary to achieve full oxidation to carbon dioxide and water. As incomplete oxidation occurs, a mixture of aldehydes, alcohols, carboxylic acids, ketones, and other partially oxidized organic species is produced by the reactor. Often, photocatalytic reactors can actually increase the overall concentration of organic contaminants in the air by fractioning large organic molecules into multiple small organic molecules such as formaldehyde.

Methods of vaporizing aqueous hydrogen peroxide solutions produce, at best, hydrated forms of hydrogen peroxide. Also, though photocatalytic systems are capable of producing hydrogen peroxide, they have multiple limitations that severely inhibit PHPG production for release into the environment. We have previously disclosed methods and devices for producing PHPG in U.S. application Ser. No. 12/187,755, published May 1, 2012, as U.S. Patent Publication No. 2009/0041617, and hereby incorporated by reference in its entirety.

FIELD OF THE DISCLOSURE

The present application provides for and includes improved devices and methods for generating Purified Hydrogen Peroxide Gas (PHPG).

SUMMARY OF THE INVENTION

The present disclosure provides for, and includes, improved devices for producing non-hydrated purified hydrogen peroxide gas (PHPG) comprising an enclosure, an air distribution mechanism providing an airflow, an air-permeable substrate structure having a catalyst on its surface, a source of light, wherein the airflow is through said air-permeable substrate structure and the device produces PHPG and directs it out of said enclosure when in operation.

The present disclosure provides for, and includes, a device for producing non-hydrated purified hydrogen peroxide gas (PHPG) when installed into a heating, ventilating, and air conditioning (HVAC) system comprising an air-permeable substrate structure having a catalyst on its surface and a source of light wherein air flows from the HVAC system through the air-permeable substrate structure and the device produces PHPG and directs it away from the air-permeable substrate structure when in operation and into a heated, ventilated and air conditioned space.

DETAILED DESCRIPTION

Figure 1A:
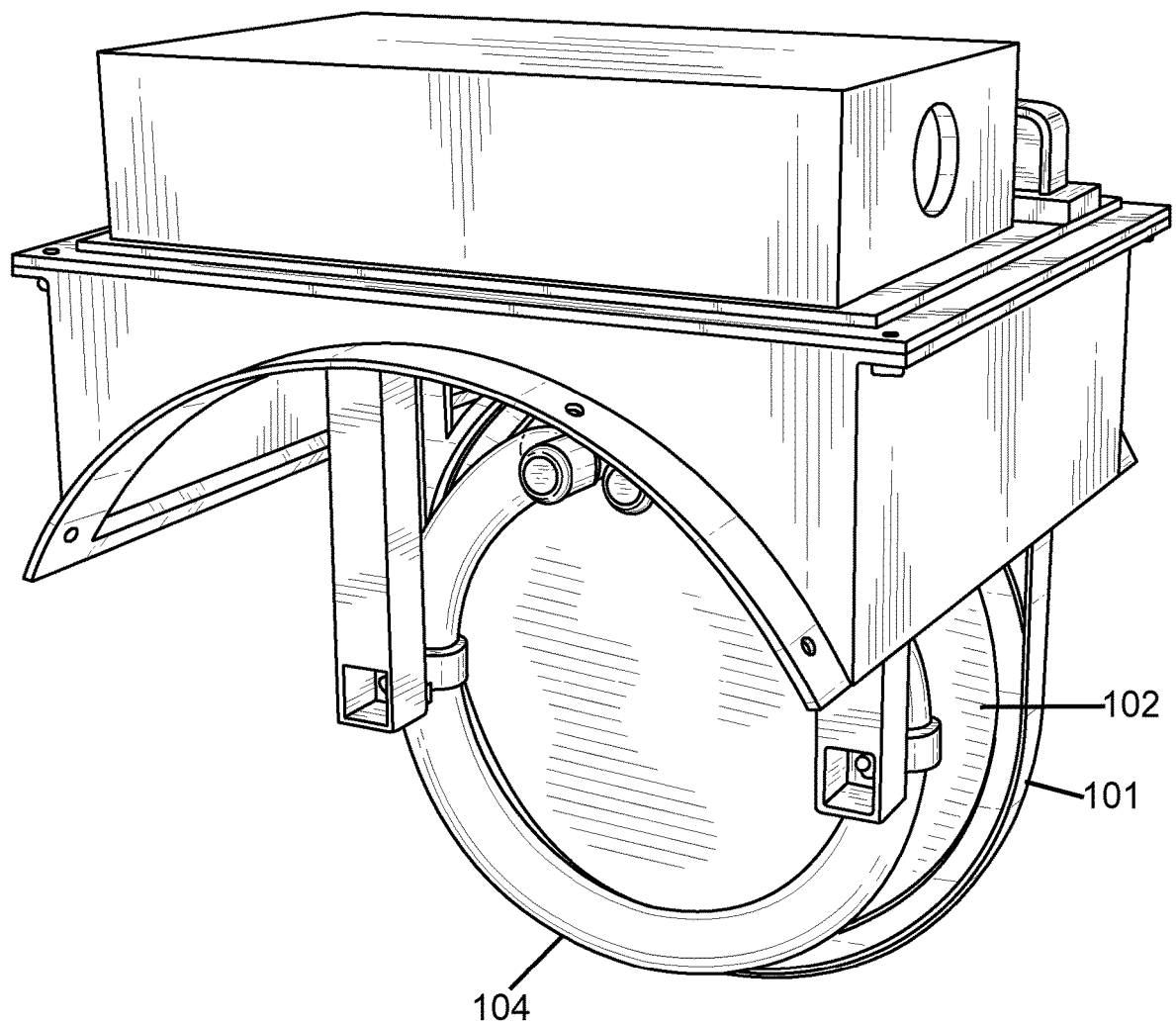
FIGS. 1A to 1C are illustrations of an embodiment of the present disclosure designed to be installed as part of an HVAC system. Notably, the enclosure and air distribution mechanism are provided by the HVAC system (e.g., the ductwork and system fans respectively).

Before explaining aspects of the invention in detail, it is to be understood that the invention is not necessarily limited in its application to the details set forth in the following description or exemplified by the Examples. The invention is capable of other aspects or of being practiced or carried out in various ways.

The present disclosure provides for and includes devices for producing non-hydrated purified hydrogen peroxide gases (PHPG). In aspects according to the present disclosure, a device for producing non-hydrated purified gas includes an enclosure, an air distribution mechanism, a source of ultraviolet light, an air-permeable substrate structure having a catalyst on its surface wherein the airflow passes through the air-permeable substrate structure and directs the PHPG produced by the device out of the enclosure when the device is in operation.

In aspects according to the present disclosure, the device produces PHPG and directs the PHPG gas out of the enclosure. Not to be limited by theory, the production of PHPG gas is rate limited and governed by the rate of adsorption of humidity from the air onto the active sites for the catalyst. Accordingly, the maximal rate of PHPG gas production is believed to be humidity dependent and can be calculated assuming the following conditions: 1. a fully hydrated catalyst; 2. sufficient light intensity to provide full activation of the catalyst; 3. 100% production with no losses due to hydrogen peroxide photolysis or hydrogen peroxide decomposition; and 4. a large excess of oxygen to be reduced. Since two photons produce two hydroxyl radicals, two free electrons, and two hydrogen ions, and an oxygen molecule is readily available, two hydrogen peroxide molecules are produced. Therefore the ratio of photons used to hydrogen peroxide molecules produced is 1:1 under wildly ideal circumstances. On a P25 grade of $TiO_2$ there are up to $14 \times 10^{14}$ active sites per square centimeter. On a P90 grade of $TiO_2$ there are up to $42 \times 10^{14}$ active sites per square centimeter. So, at best, a fully hydrated catalyst can produce $42 \times 10^{14}$ molecules of hydrogen peroxide immediately using adsorbed water. After that, the rate of production will be governed by the rate at which new water is adsorbed onto the catalyst, which is humidity dependent.

In another aspect, the device produces PHPG at a rate sufficient to establish a steady state concentration of PHPG of at least 0.005 ppm in a closed air volume of 10 cubic meters.

In an aspect, the device produces a concentration of at least 0.005 ppm in an air volume of 10 cubic meters ($m^3$) wherein 10 percent of the air volume is replaced with fresh, non-PHPG containing air each hour.

In aspects according to the present disclosure, hydrogen peroxide gas may be measured in a volume of air. Since no device is yet readily available to measure hydrogen peroxide gas at levels below 0.10 ppm, methods to measure the amount of hydrogen peroxide over time or methods employing a calibrated pump may be employed. In an aspect, a hydrogen peroxide test strip normally used to measure approximate concentrations in aqueous solution can be used to detect the presence of PHPG over time. In an aspect, a hydrogen peroxide test strip can measure the accumulated PHPG up to one hour to provide approximate readings of PHPG concentration accurate to within 0.01 ppm. In certain aspects, a test strip that accumulates 0.5 ppm over the course of five minutes when exposed for 15 twenty-second intervals, indicates an approximate concentration of 0.033 ppm (e.g., 0.5 ppm divided by 15). In other aspects, a Draeger tube, designed to detect hydrogen peroxide concentrations as low as 0.10 ppm after drawing 2000 cubic centimeters of air using a calibrated pump, provides readings of lower concentrations accurate within 0.005 ppm using larger volumes of air for measurement. In certain aspects, a Draeger tube indicating a measure of PHPG at 0.10 ppm after drawing in 4000 cubic centimeters provides a concentration of 0.05 ppm. In another aspect, a Draeger tube that indicated 0.10 ppm after drawing 6000 cubic centimeters, measures an approximate PHPG concentration of 0.033 ppm.

According to the present disclosure, non-hydrated purified hydrogen peroxide gas (PHPG) comprises gaseous hydrogen peroxide ($H_2O_2$) that is substantially free of hydration, ozone, plasma species, or organic species.

As used herein, the term "substantially free of ozone" means an amount of ozone below about 0.015 ppm ozone.

In an aspect, "substantially free of ozone" means that the amount of ozone produced by the device is below or near the level of detection (LOD) using conventional detection means. Ozone detectors are known in the art and have detection thresholds in the parts per billion using point ionization detection. A suitable ozone detector is the Honeywell Analytics Midas® gas detector capable of detecting 0.036 to 0.7 ppm ozone.

As used herein, substantially free of hydration means that the hydrogen peroxide gas is at least 99% free of water molecules bonded by electrostatic attraction and London Forces.

Also as used herein, a PHPG that is substantially free of plasma species means hydrogen peroxide gas that is at least 99% free of hydroxide ion, hydroxide radical, hydronium ion, and hydrogen radical.

As used herein the term "higher" refers to at least about 3%, 5%, 7%, 10%, 15%, 20%, 25%, 30%, 50%, 60%, 70%, 80%, 90%, or even a few folds higher.

As used herein the term "improving" or "increasing" refers to at least about 2%, at least about 3%, at least about 4%, at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, or greater increase.

As used herein the term "about" refers to ±10%.

The terms "comprises," "comprising," "includes," "including," "having," and their conjugates mean "including but not limited to."

The term "consisting of" means "including and limited to."

The term "consisting essentially of" means that the composition, method, or structure may include additional ingredients, steps, and/or parts, but only if the additional ingredients, steps, and/or parts do not materially alter the basic and novel characteristics of the claimed composition, method, or structure.

As used herein, the singular form "a," "an," and "the" include plural references unless the context clearly dictates otherwise. For example, the term "a compound" or "at least one compound" may include a plurality of compounds, including mixtures thereof.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals there between.

As used herein the term "method" refers to manners, means, techniques, and procedures for accomplishing a given task including, but not limited to, those manners, means, techniques, and procedures either known to or readily developed from known manners, means, techniques, and procedures by practitioners of the agronomic, chemical, pharmacological, biological, biochemical, and medical arts.

In aspects according to the present disclosure, an enclosure comprises a volume having at least one opening for the entry of air and at least one opening for the discharge of air having non-hydrated purified hydrogen peroxide gas. In an aspect, the enclosure may be made of plastic, metal, wood, or glass. According to some aspects, the enclosure may be opaque. In other aspects, the enclosure may be opaque to ultraviolet light and provide for the transmission of light in the visible spectrum. In an aspect, the enclosure may further include a reflective surface on the inside of the device to reflect light back to the air-permeable substrate structure having a catalyst and thereby increase the production of non-hydrated purified hydrogen peroxide gas. In an aspect, an enclosure may comprise a material resistant to degradation by ultraviolet light. In aspects according to the present disclosure, the enclosure may be prepared from plastics selected from the group consisting of acrylic, polyester, silicone, polyurethane, and halogenated plastic. In some aspects, the enclosure may be prepared from a ceramic or porcelain. In some aspects, the enclosure may be prepared from polyethylene, polypropylene, polystyrene, nylon, or polyvinyl chloride.

Figure 1B:
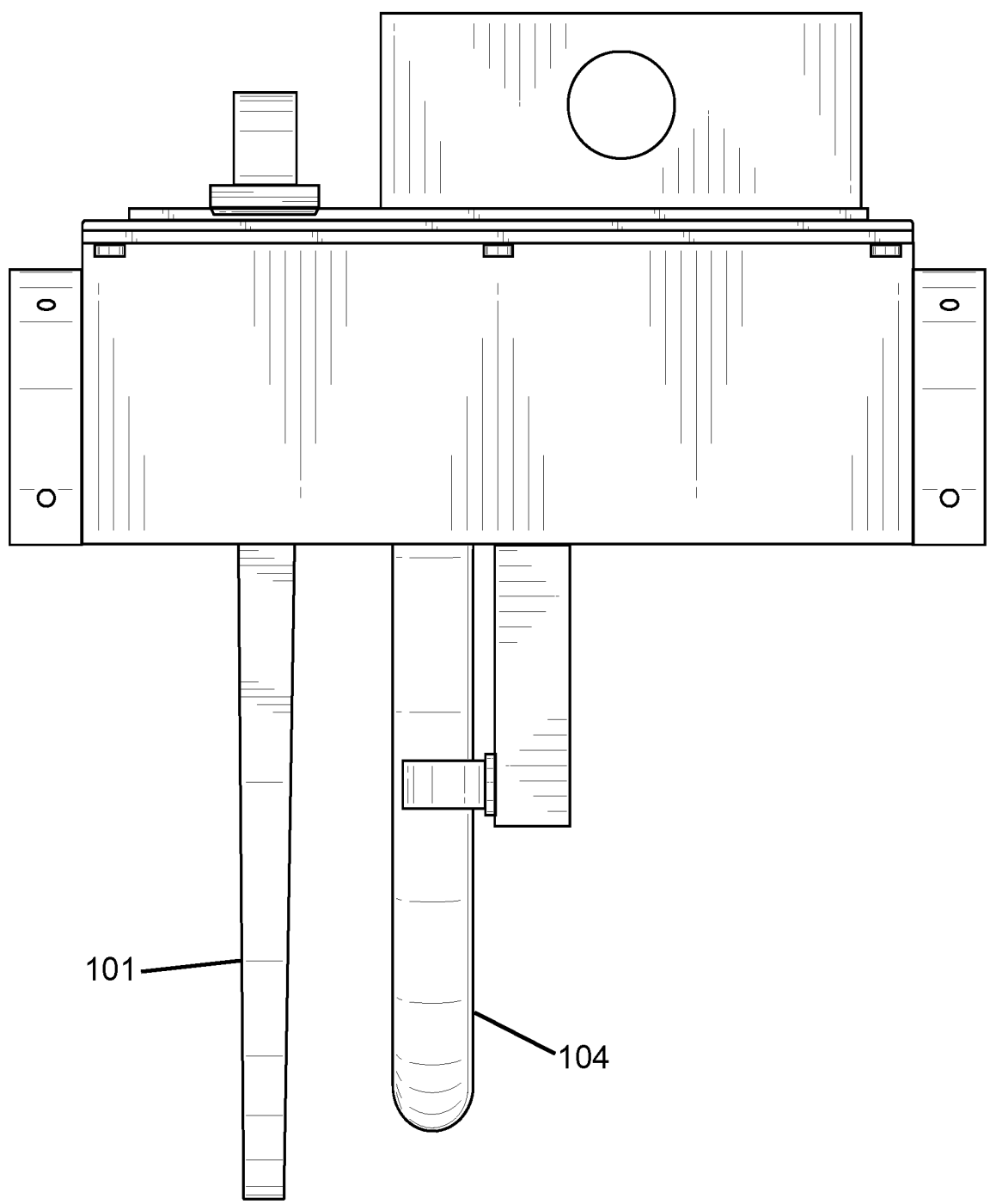
Figure 1C:
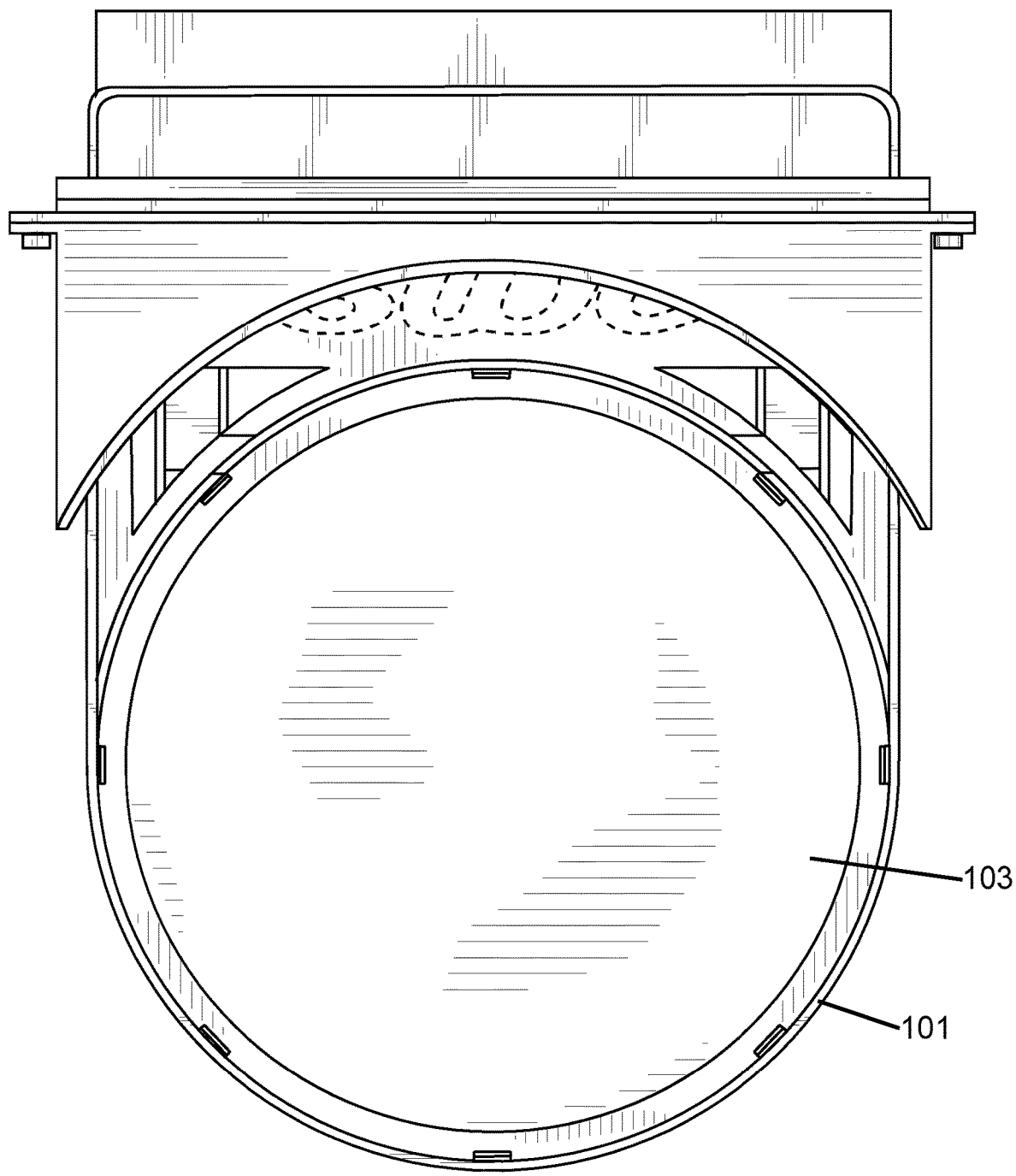

As used herein, in other aspects, an enclosure can comprise a heating, ventilating, and air conditioning (HVAC) system. Referring to FIGS. 1A to 1C, a device for producing PHPG is a device placed within an existing HVAC system comprising an air-permeable substrate structure 102 having a catalyst on its surface and a source of light 104 as recited below In other aspects, a device for producing PHPG is a device placed in an HVAC system during construction. An aspect of a PHPG producing device suitable for incorporation into an HVAC system is illustrated in FIGS. 1A to 1C. As illustrated, a suitable device can be installed into an existing HVAC system that having a rectangular duct according to applicable national and international standards. Suitable HVAC systems and appropriate standards are known in the art, for example standards developed by the Sheet Metal & Air Conditioning Contractors' National Association (SMACNA). For example, the American National Standards Institute (ANSI) has accredited SMACNA as a standard-setting organization. As provided herein, devices suitable for installation into an HVAC system include the elements recited for standalone devices but wherein the enclosure and air distribution system are provided by the HVAC system. Devices suitable for installation into an HVAC system may further comprise an additional air distribution system (e.g., separate from the air distribution system of the HVAC system as a whole). Devices suitable for installation into an HVAC system may further comprise one or more additional filters to prevent contamination with dust or chemicals.

In aspects according to the present disclosure, a device includes an air distribution mechanism to provide an airflow. In some aspects, the air flow is a continuous airflow. In other aspects, the air flow is discontinuous. In aspects according to the present disclosure, the airflow of the device may be a laminar flow of air though an air-permeable substrate structure. In other aspects, the airflow may be turbulent flow through an air-permeable substrate. In yet another aspect, the airflow may be transitional. In aspects according to the present disclosure, the airflow of the device may have a Reynolds number of less than 2300. In another aspect, the airflow of the device may have a Reynolds number of between 2300 and 4000. In yet another aspect, the airflow of the device may have a Reynolds number of greater than 4000.

In some aspects, an air distribution mechanism is placed upstream of an air permeable substrate structure and provides an airflow through the air permeable substrate. In other aspects, an air distribution mechanism is placed after an air permeable substrate and pulls the air through the substrate. In certain aspects, the airflow is provided by one or more fans. In certain aspects, the airflow may be provided by a source of compressed air. In an aspect, the source of compressed air may be a tank of compressed air. In other aspects, the compressed air may be provided by an air compressor and storage tank. In yet another aspect, the air flow is provided by a climate control system such as an air conditioner, a furnace, or a heating, ventilation, and air-conditioning (HVAC) system.

In aspects according the present disclosure, the device may provide an airflow having a velocity, a direction, and an angle of incidence relative to the air permeable substrate structure.

Devices of the present disclosure are provided with an airflow sufficient to minimize the time of contact with the photocatalytic surface. More specifically, devices of the present disclosure are designed to minimize the contact of hydrogen peroxide gas generated during photocatalysis with the photocatalytic substrate in order to minimize the degradation of the hydrogen peroxide by contaminating ozone, hydroxide ions, hydroxide radicals, hydronium ions, and hydrogen radicals. This minimization of ozone production and contact is in contrast with "air purification" filters and devices employing similar photocatalytic principles. In contrast to devices of the present disclosure, air purifiers and filters are designed to maximize the contact of the air with the catalytic surface and the photocatalytic plasma. Even further, prior filters and purifiers are designed to act within an enclosed volume and are designed not to expel PHPG but rather 'clean' air having volatile organic compounds (VOC's), bacteria, microbes, spores, viruses, and other undesirable contaminants destroyed or reduced. Similarly, prior filters and purifiers are concerned with the production of ozone and/or hydroxide radicals, each of which is undesirable in devices of the present disclosure.

The devices of the present disclosure include and provide for air distribution mechanisms capable of providing an airflow having a velocity from about 5 nanometers/second (nm/s) to 10,000 nm/s as measured at the surface of the air permeable substrate structure. In certain aspects, the flow rate is between 5 nm/s to 7,500 nm/s. In certain aspects, the flow rate is between 5 nm/s to 5,000 nm/s. In certain aspects, the flow rate is between 5 nm/s to 2,500 nm/s. In certain aspects, the flow rate is between 5 nm/s to 5,000 nm/s. In certain aspects, the flow rate is between 5 nm/s to 1,000 nm/s. In other aspects, the flow rate of the air at the air permeable substrate structure is between 5 and 15 nm/s. In another aspect, the air flow velocity is between 15 nm/s to 30 nm/s. In an aspect, the air flow velocity is between 30 nm/s to 50 nm/s. In an aspect, the air flow velocity is between 50 nm/s to 75 nm/s. In an aspect, the air flow velocity is between 75 nm/s to 100 nm/s. In an aspect, the air flow velocity is between 100 nm/s to 250 nm/s. In an aspect, the air flow velocity is between 250 nm/s to 500 nm/s. In an aspect, the air flow velocity is between 500 nm/s to 750 nm/s. In an aspect, the air flow velocity is between 750 nm/s to 1000 nm/s. In an aspect, the air flow velocity is between 1000 nm/s to 2,500 nm/s. In an aspect, the air flow velocity is between 2,500 nm/s to 5,000 nm/s. In an aspect, the air flow velocity is between 5,000 nm/s to 7,500 nm/s. In an aspect, the air flow velocity is between 7,500 nm/s to 10,000 nm/s. As provided herein, the maximal airflow through the air permeable structure is limited by the reaction of hydroxyl radicals into hydrogen peroxide and the production rate of PHPG drops. Not to be limited by theory, it is thought that the hydroxyl radicals are maintained in a sufficiently dilute balance which favors their combination to form hydrogen peroxide yet minimizes decomposition into water and oxygen. The maximal flow limitation depends on the air permeable structure, the catalyst, the relative humidity and other variables and one of ordinary skill in the art can readily adjust the airflow to maximize PHPG production. In certain aspects, suitable devices for HVAC systems are designed to handle air flows up to 40,000 cubic feet per minute (CFM).

The present disclosure provides for, and includes, airflow rates through the air permeable substrate structure of greater than 100 CFM. In an aspect, PHPG generating devices for an HVAC system are provided an airflow on average of 145 CFM. For a standalone PHPG generating device, the air distribution mechanism provides for an average of 115 CFM through the air permeable substrate structure.

The present disclosure also includes and provides for devices having an air flow velocity sufficient to provide a residence time on the catalyst surface of less than 1 second. One of ordinary skill in the art would understand that the time available at a catalyst surface is affected by, among other parameters, the air velocity, the angle of incidence, and the thickness of the substrate. In aspects according to the present disclosure, the device provides a residence time on the catalyst surface of an air permeable substrate of less than 2 seconds. In an aspect, the residence time is less than 1 second. In some aspects, the residence time is less than 500 ms. In a further aspect, the residence time is less than 250 ms. In yet another aspect, the residence time is between 1 and 500 ms.

In aspects, the direction of the airflow at the air permeable structure may be provided at an angle relative to the air permeable structure (the angle of incidence). In contrast to the present disclosure, the PHPG producing devices disclosed in U.S. Pat. Nos. 8,168,122, 8,684,329 and 9,034,255, provide a diffuser apparatus for producing non-hydrated purified peroxide gas (PGPG) from humid ambient air having an airflow perpendicular to a thin air permeable substrate structure. Here, we show that production of PHPG can be achieved using air flows that are incident to the air permeable substrate at angles of at least 14°. Not to be limited by theory, the permissible angle of incidence is believed to be related to the thickness of the air permeable substrate structure and the velocity of airflow. As the thickness of the substrate structure is reduced, the incident angle may also be reduced, starting at 90° (airflow to substrate angle) which provides the optimal condition for the production of PHPG by maintaining a short residence time of hydrogen peroxide on the substrate surface. Similarly, the angle of incidence may be reduced for a given thickness of substrate as the velocity of the airflow is increased, though angles below 14° did not result in the production of detectable levels of PHPG. Not to be limited by theory, the rate of PHPG production is maximal at an angle of incidence of 90° and essentially non-detectable when the angle of incidence of the airflow is at about 14 degrees or less. Between about 14° C. and 68° C., the production of PHPG increases steadily. Unexpectedly, at angles of incidence as low as 68° C. suitable levels of PHPG are produced, and consistent with previous reports, optimal production occurs when the airflow is perpendicular. Accordingly, devices in the art that have catalytic surfaces that are parallel to the airflow do not produce PHPG, even if the incident light is perpendicular. Thus, devices in the art designed to generate ozone, peroxide and other reactive species within a reactor do not produce PHPG and do not direct PHPG outside of the reactor.

In certain aspects, the airflow may be provided at an incident angle of 90° relative to the air permeable substrate structure (e.g., perpendicular to the air permeable substrate). In devices having an incident angle of 90°, the residence time of the non-hydrated purified hydrogen peroxide gas is minimal for a given airflow and substrate thickness. In aspects according to the present disclosure, the minimal incident angle is 14°. In other aspects, the incident angle of the airflow relative to the air permeable structure is at least 45° or greater. In another aspect, the incident angle is greater than 50°. In yet another aspect, the incident angle is greater than 60°. In a further aspect, the incident angle is greater than 70°. In another aspect, the incident angle is greater than 75°. In an aspect, the incident angle may be greater than 80°. In a further aspect, the incident angle may be greater than 85°. In yet another aspect, the incident angle may be greater than 89°. In aspects according to the present disclosure, the incident angle of the airflow may be between 68° and 90° relative to the substrate structure. In other aspects, the incident angle of the airflow may be between 75° and 90° relative to the substrate structure. In other aspects, the incident angle of the airflow may be between 85° and 90° relative to the substrate structure.

In aspects according to the present disclosure, the airflow through the air permeable substrate structure is humid air. In certain aspects, the humid air is ambient humid air. In other aspects, the humidity of the air flowing through the air permeable substrate is at or above 20% RH. In further aspects, the humidity of the air flowing through the air permeable substrate is at or above 30%. In some aspects, the relative humidity is between 35% and 40%. In other aspects, the humidity of the ambient air may be between about 20% and about 99% RH. In other aspects, the humidity of the ambient air may be between about 20% and about 99% RH. In certain aspects, the humidity of the air flow is less than 80%. In an aspect, the humidity is between 20% and 80%. In yet other aspects, the relative humidity is between 30% and 60%. In another aspect, the humidity is between 35% and 40%. In some aspects, the humidity of the air flowing through the air permeable substrate structure is between 56% and 59%. In aspects according to the present disclosure the relative humidity is between 20% and 80%.

In aspects according to the present disclosure, the airflow through the air permeable substrate structure may be supplemented by humidification. In certain aspects, ambient air is supplemented by a humidifier to provide an airflow having at least 20% humidity. In certain aspects, the relative humidity of the air flowing through permeable substrate structure is maintained at between 20% and 80%. In another aspect, the air may be humidified to 30% or higher relative humidity. In some aspects, the relative humidity of the humidified airflow is between 35% and 40%. In other aspects, the humidity of the humidified air may be between about 20% and about 99% or between about 30% to 99% RH. In an aspect, the relative humidity after humidification is less than 80%. In an aspect, the relative humidity after humidification is between 20% and 80%. In yet other aspects, the relative humidity after humidification is between 30% and 60%. In another aspect, the relative humidity after humidification is between 35% and 40%. In some aspects, the relative humidity after humidification of the air flowing through the air permeable substrate structure is between 56% and 59%.

In aspects according to the present disclosure, a device may provide an airflow that recirculates air within a space. In other aspects, a device may provide, in whole or in part, an airflow comprising fresh air. In certain aspects, the device includes and provides for a source of fresh air either from the outside or from a separate filtered flow of air. In aspects according to the present disclosure, the device may be included in an air conditioning and ventilation system that recirculates air within a room or building. In some aspects, the recirculating room or building air may be supplemented with fresh outside air.

The devices of the present disclosure include an air permeable substrate structure having a catalyst on the surface configured to produce non-hydrated purified hydrogen peroxide gas when exposed to a light source and provided an airflow. The substrate structure can vary in thickness, air permeability, and surface catalyst. In certain aspects, the substrate structure may be thicker or thinner depending on the rate of air flow, the incident angle of the air flow, the intensity of the light, and the type of catalyst. The selection of thickness, air flow, air flow angle, and other parameters is to provide a substrate surface morphology to minimize the residence time of hydrogen peroxide molecules on the surface of the air permeable substrate structure. Not to be limited by theory, it is thought that hydrogen peroxide gas generated on the substrate surface is released from the surface and thereby prevented from being reduced back into water by the substrate or hydroxide.

In aspects according to the present disclosure, the air permeable substrate structure having a catalyst on its surface is between about 5 nanometers (nm) and about 750 nm in total thickness. In certain aspects, the maximum thickness of an air permeable substrate structure is 650 nm. In an aspect, the thickness of the air permeable substrate structure is between 100 and 200 nm. In an aspect, the thickness of the air permeable substrate structure is between 145 and 150 nm. In an aspect, the thickness of the air permeable substrate structure is between 5 nm and 15 nm. In another aspect, the thickness of the air permeable substrate structure is between 15 nm and 30 nm. In an aspect, the thickness of the air permeable substrate structure is between 20 nm and 40 nm. In an aspect, the thickness of the air permeable substrate structure is about 30 nm. In a further aspect, the thickness of the air permeable substrate structure is between 30 nm and 50 nm. In yet another aspect, the thickness of the air permeable substrate structure is between 50 nm and 75 nm. In an aspect, the thickness of the air permeable substrate structure is between 75 nm and 100 nm. In yet another aspect, the thickness of the air permeable substrate structure is between 100 nm and 250 nm. In a further aspect, the thickness of the air permeable substrate structure is between 250 nm and 500 nm. In certain aspects, the thickness of the air permeable substrate structure is between 500 nm and 750 nm. In aspects according to the present disclosure, the thickness of the air permeable substrate structure having a catalyst on its surface is between about 5 nm and 100 nm. In an aspect, the thickness of the air permeable substrate structure having a catalyst on its surface is between about 15 nm and 100 nm. In an aspect, the thickness of the air permeable substrate structure having a catalyst on its surface is between about 20 nm and 100 nm. In an aspect, the thickness of the air permeable substrate structure having a catalyst on its surface is between about 20 nm and 75 nm. In an aspect, the thickness of the air permeable substrate structure having a catalyst on its surface is between about 20 nm and 50 nm.

In certain aspects according to the present disclosure, the air permeable substrate structure having a catalyst on its surface is between about 750 nanometers (nm) and about 1000 nm in total thickness. In an aspect, the thickness of the air permeable substrate structure is between 1000 and 2500 nm. In another aspect, the thickness of the air permeable substrate structure is between 2500 nm and 5000 nm. In an aspect, the thickness of the air permeable substrate structure is between 5000 nm and 7500 nm. In a further aspect, the thickness of the air permeable substrate structure is between 7500 nm and 10000 nm.

Also provided for and included in the present disclosure are devices having an air permeable substrate structure configured as a mesh. As used herein, a "mesh" refers to a network of spaces in a net or network comprising a network of cords, threads, or wires. In some aspects, a mesh may be a woven cloth or fabric. In some aspects, a mesh may be a woven stainless steel. In certain aspects, a mesh may be a woven stainless steel shaped as honeycombs. In other aspects, a mesh may be a nonwoven cloth or fabric. In certain aspects, a mesh may be prepared from a solid sheet by introducing holes or perforations either mechanically, thermally, or chemically. In an aspect, a mesh may be prepared from a film.

In the course of developing devices of the present disclosure, it is observed that air permeable substrate structures require a mesh having at least 20% open area in order to generate effective amounts of PHPG. Similarly, when the open area of the mesh is greater than 60%, PHPG generation is essentially eliminated. Accordingly, the present disclosure provides for and includes, air permeable substrate structures having a mesh with an open area of between 20% and 60% and a maximal thickness of up to 750 nm. Suitable thicknesses of air permeable substrates are provided above. Also included are air permeable substrate structures having a mesh with an open area of about 40%. In an aspect the mesh opening is about 200 microns and the thread thickness is about 152 microns.

Additional testing revealed that non-woven fabrics are not suitable for the preparation of air permeable substrates coated with a catalyst. Not to be limited by theory it is thought that the inability to identify suitable non-woven materials results from the irregular or insufficient mesh of the non-woven materials. However, it is believed that suitable non-woven materials can be prepared. Accordingly, included and provide by the present disclosure are non-woven air permeable substrate structures having a mesh of between 20 and 60% and a thickness of less than 750 nm that are useful in the preparation of PHPG generating devices.

In aspects according to the present disclosure, a mesh is greater than 20 strands per centimeter. In certain aspects, the open area of the mesh is less than about 120 strands per centimeter. In an aspect, the mesh opening is about 200 microns (μm) corresponding to about 41% open area for a thread thickness of about 150 microns. In certain aspects, the mesh includes an open area of at least about 20% and a thread thickness of about 48 microns. In certain aspects, the mesh has a hole size of between 25 μm and 220 μm and having an open area of between 20% and 40%. In other aspects, the mesh has a hole size of between 25 μm and 220 μm and a thread thickness of between 48 μm and 175 μm.

In aspects according to the present disclosure, a mesh may be prepared having a regular, repeating pattern of spaces in the net or network. In other aspects, a mesh of the present disclosure may have an irregular or non-repeating pattern of spaces. In yet another aspect, the mesh may be a random array of open spaces. In another aspect, the mesh may have a honeycomb appearance. In aspects according to the present disclosure, the open spaces within the mesh are round, triangular, square, polygonal, polyhedron, ellipsoid, or spherical.

An air permeable substrate structure of the present disclosure can be prepared from a number of suitable materials. In certain aspects, an air permeable substrate structure may comprise a catalyst. In other aspects, an air permeable substrate structure may comprise a catalyst and a co-catalyst. In yet other aspects, an air permeable substrate structure may comprise a catalyst, a co-catalyst, and an additive. In certain aspects, an air permeable substrate structure may be prepared as a ceramic. In yet other aspects, the air permeable substrate structure consists solely of the catalyst or catalyst/co-catalyst combination.

The present disclosure also provides for air permeable substrates that are coated. In some aspects, an air permeable substrate structure may comprise a material that is coated with one or more catalysts. In other aspects, an air permeable substrate structure may comprise a material that is coated with a catalyst and one or more co-catalysts. In yet another aspect, an air permeable substrate structure may comprise a material that is coated with a mixture of a catalyst, co-catalyst, and an additive.

Methods for coating an air permeable substrate are known in the art. In certain aspects, an air permeable substrate is coated with a crystalline titanium dioxide powder in one or more applications and sintered in an oven. The coatings of the present disclosure may be applied to a mesh by a variety of methods including, but not limited to, gel sol methods, painting, dipping, and powder coating. In other aspects, the catalysts, co-catalysts and additives of the present disclosure may be applied to a mesh by toll coating, tape casting, ultrasonic spray and web-based coating. As provided herein, the method of applying the catalysts, co-catalysts and additives is suitable if it provides for, and includes, retaining the mesh of the underlying air permeable substrate as recited above.

According to the present disclosure, an air permeable substrate structure comprises a mesh having a percentage of open area of between 20% and 60% after coating. In another aspect, the mesh may have an open area of between 20% and 30%. In an aspect, the mesh may have an open area of between 30% and 40%. In a further aspect, the mesh may have an open area of between 40% and 50%. In yet another aspect, the mesh may have an open area of between 50% and 60%. In certain aspects, the percentage of open area of the mesh may be between 36% and 38%. In an aspect, the percentage of open area is about 37%.

The present disclosure provides for and includes for air permeable substrate structures having a thickness of between 5 nm and 750 nm and having an open area of a mesh between 10% and 60%. In an aspect, the substrate structure may have a thickness selected from the group consisting of 5 nm to 15 nm, 15 nm to 30 nm, 20 nm to 40 nm, 30 nm to 50 nm, 50 nm to 75 nm, 75 nm to 100 nm, 100 nm to 250 nm, 250 nm to 500 nm, and 500 nm to 750 nm and having an open area of mesh between 10% and 20%. In an aspect, the substrate structure may have a thickness selected from the group consisting of 5 nm to 15 nm, 15 nm to 30 nm, 20 nm to 40 nm, 30 nm to 50 nm, 50 nm to 75 nm 75 nm to 100 nm, 100 nm to 250 nm, 250 nm to 500 nm, and 500 nm to 750 nm thick and has an open area of mesh between 20% and 30%. In an aspect, the substrate structure may have a thickness selected from the group consisting of 5 nm to 15 nm, 15 nm to 30 nm, 20 nm to 40 nm, 30 nm to 50 nm, 50 nm to 75 nm, 75 nm to 100 nm, 100 nm to 250 nm, 250 nm to 500 nm, and 500 nm to 750 nm thick and has an open area of mesh between 30% and 40%. In an aspect, the substrate structure may have a thickness selected from the group consisting of 5 nm to 15 nm, 15 nm to 30 nm, 20 to 40 nm, 30 nm to 50 nm, 50 nm to 75 nm, 75 nm to 100 nm, 100 nm to 250 nm, 250 nm to 500 nm, and 500 nm to 750 nm thick and has an open area of mesh between 40% and 50%. In an aspect, the substrate structure may have a thickness selected from the group consisting of 5 nm to 15 nm, 15 nm to 30 nm, 20 to 40 nm, 30 nm to 50 nm, 50 nm to 75 nm, 75 nm to 100 nm, 100 nm to 250 nm, 250 nm to 500 nm, and 500 nm to 750 nm thick and has an open area of mesh between 50% and 60%. In an aspect, the substrate structure may have a thickness selected from the group consisting of 5 nm to 15 nm, 15 nm to 30 nm, 20 nm to 40 nm, 30 nm to 50 nm, 50 nm to 75 nm, 75 nm to 100 nm, 100 nm to 250 nm, 250 nm to 500 nm, and 500 nm to 750 nm thick and has an open area of mesh between 36% and 38%.

In other aspects, the air permeable substrate structure has a thickness of between 15 nm and 250 nm and has an open area of a mesh between 20% and 50%. In another aspect, the air permeable substrate structure has a thickness of between 15 nm and 100 nm and has an open area of a mesh between 20% and 50%. In another aspect, the air permeable substrate structure has a thickness of between 20 nm and 80 nm and has an open area of a mesh between 20% and 50%. In another aspect, the air permeable substrate structure has a thickness of between 20 nm and 50 nm and has an open area of a mesh between 20% and 50%. In another aspect, the air permeable substrate structure has a thickness of between 20 nm and 40 nm and has an open area of a mesh between 20% and 50%.

In other aspects, the air permeable substrate structure has a thickness of between 15 nm and 250 nm and has an open area of a mesh between 30% and 50%. In another aspect, the air permeable substrate structure has a thickness of between 15 nm and 100 nm and has an open area of a mesh between 30% and 50%. In another aspect, the air permeable substrate structure has a thickness of between 20 nm and 80 nm and has an open area of a mesh between 30% and 50%. In another aspect, the air permeable substrate structure has a thickness of between 30 nm and 50 nm and has an open area of a mesh between 30% and 50%. In another aspect, the air permeable substrate structure has a thickness of between 20 nm and 40 nm and has an open area of a mesh between 30% and 50%.

In other aspects, the air permeable substrate structure has a thickness of between 20 nm and 40 nm and has an open area of a mesh between 10% and 60%. In another aspect, the air permeable substrate structure has a thickness of between 20 nm and 40 nm and has an open area of a mesh between 20% and 50%. In another aspect, the air permeable substrate structure has a thickness of between 20 nm and 40 nm and has an open area of a mesh between 30% and 40%. In another aspect, the air permeable substrate structure has a thickness of between 20 nm and 40 nm and has an open area of a mesh between 36% and 38%. In another aspect, the air permeable substrate structure has a thickness of between 20 nm and 40 nm and has an open area of a mesh of about 37%.

Air permeable substrates suitable for coating with a catalyst mixture of the present disclosure are known in the art. In certain aspects, an air permeable substrate comprises a solid sheet that is coated with a catalyst or catalyst containing mixture and then rendered air permeable by the introduction of holes or perforations as provided above. In other aspects, an air permeable substrate comprises a solid sheet that has been perforated and is subsequently coated with a catalyst or catalyst mixture.

Suitable air permeable substrates for coating with a catalyst mixture according to the present disclosure include meshes, such as woven cloth or fabric or unwoven cloth or fabric. As provided herein, coating of a suitable mesh with a catalyst mixture requires that the mesh not be occluded and that the mesh retain an open area of between 20% and 60% as provided above.

Air permeable substrates of the present disclosure may be prepared from polymers, carbon fibers, fiberglass, natural fibers, metal wires, and other materials that can be prepared as a mesh. Meshes may be woven meshes prepared from monofilament synthetic or natural fibers or yarns. In other aspects, woven meshes may be prepared from multifilament synthetic fibers or yarns. Woven meshes of the present disclosure may be described by the thread count and have a thread diameter. Woven meshes comprise warp threads that run lengthwise in a woven mesh or fabric, and weft or filling threads that run across the width of a fabric at right angles to the warp thread. In woven meshes comprising monofilaments, equal diameter threads and equal thread counts are present in both the warp and weft directions and square mesh openings (or holes). Monofilament woven meshes may have different numbers of thread counts in the warp and weft direction resulting in rectangular mesh openings. Woven meshes are available in a wide variety of thread counts.

Woven monofilament meshes suitable for devices of the present disclosure comprise meshes having nominal hole sizes (e.g., mesh openings) ranging from 50 microns to 1200 microns. In an aspect, the woven monofilament mesh suitable for coating as an air permeable substrate has a mesh opening of between 100 and 300 microns. In another aspect, an air permeable substrate is a woven monofilament mesh having an opening of between 150 and 250 microns. In yet another aspect, an air permeable substrate is a woven monofilament mesh having a mesh opening of about 200 microns. In an aspect, the woven monofilament mesh opening of between 175 and 225 microns and a tread thickness of between 125 and 175 microns. In yet another aspect, the woven monofilament mesh opening of about 200 microns and a tread thickness of about 152 microns.

In aspects according to the present disclosure, a mesh may be an extruded mesh (also called "extruded netting"). In an aspect, an extruded mesh may be a bi-planar extruded mesh. In another aspect, the extruded mesh may be a mono-planar mesh. Extruded mesh may comprise a netting having a variety of apertures (hole sizes), weights, and thicknesses. Extruded meshes may be prepared from polypropylene (PP), polyethylene (PE), high density polyethylene (HDPE), medium-density polyethylene (MDPE), low-density polyethylene (LDPE), polypropylene/polyethylene (PP/PE) blends, cross-linked polyethylene (PEX), ultra-high molecular weight polyethylene (UHMWPE).

In an aspect, a mesh suitable for coating according to the present disclosure is a fiberglass mesh or cloth. In some aspects, the fiberglass mesh is a fiberglass reinforced plastic (FRP). In some aspects, the fiberglass mesh is a woven mesh. Suitable woven fiberglass meshes include fiberglass cloth, fiberglass chopped strand mat, woven rovings. In some aspects, a fiberglass cloth is a combination of woven roving and chopped strand mat. In another aspect, a fiberglass cloth is S-2 GLASS™. In some aspects, the fiberglass cloth is prepared using a plain weave, long shaft satin weave, unidirectional weave, or twill weave. In an aspect, a fiberglass cloth comprises E-glass. In another aspect, a fiberglass cloth comprises C-glass. In yet another aspect, a fiberglass cloth comprises E-glass and C-glass. In some aspects, a fiberglass mesh or cloth is combined with a resin to reinforce the fiberglass material. In one aspect, the resin is polyester. In another aspect, the resin is an epoxy.

In an aspect, a mesh suitable for coating according to the present disclosure is a polymer. In an aspect the mesh may be nylon, polybutylene terephthalate (PBT), polyester, polyethylene, polypropylene, polytetrafluoroethylene (PTFE), polypropylene/polyethylene (PP/PE) blends or synthetic yarns or fibers.

In aspects according to the present disclosure, a mesh may be prepared from natural fibers including cotton and wool. In some aspects, the natural fiber is seed fiber, a leaf fiber, a bast fiber, a skin fiber, a fruit fiber, or a stalk fiber. In other aspects, the natural fiber is hemp, sisal, jute, kenaf, or bamboo. In an aspect, the mesh may be prepared from silk.

Meshes according to the present disclosure may be a metal mesh or a ceramic mesh. Suitable metal meshes include electroformed screens. Electroformed screens suitable for the preparation of catalyst coated air permeable substrates according to the present disclosure are available from, for example, Industrial Netting (Minneapolis, Minn.). Electroformed screens may have hole sizes ranging from 8 microns to 5000 microns or more. In certain aspects, the electroformed screen ranges from 36% to 98% open. In some aspects, the electroformed screen ranges from 36% to 98% open and has a thickness of between about 20 nm and 75 nm.

The devices of the present disclosure provide for, and include, a catalyst on the surface of said air permeable substrate structures. In certain aspects, a catalyst may be a catalyst mixture comprising one or more catalysts. In other aspects, a catalyst mixture may comprise one or more catalysts and one or more co-catalysts. In another aspect, a catalyst mixture may comprise one or more catalysts and one or more additives. In a further aspect, a catalyst mixture may comprise one or more catalysts, one or more co-catalysts, and one or more additives. Catalyst mixtures may further comprise solubilizer, binders, viscosity modifiers, isotonizing agents, pH regulators, solvents, dyes, gelling agents, thickeners, buffers, and combinations thereof.

One of ordinary skill in the art would understand that the selection of the catalyst determines the type of photocatalysis that occurs upon illumination with a light source and further determines the wavelength and intensity of light suitable for generating non-hydrated purified hydrogen peroxide gas. As discussed above, hydroxyl radicals produced by photocatalysis must be removed from the catalytic surface before they undergo reduction by free electrons on the catalyst or by other reactive species produced by photocatalysis. This forces them to combine to form hydrogen peroxide just beyond the catalyst. One of ordinary skill in the art would understand that the residence time of non-hydrated purified hydrogen peroxide gas on the air permeable substrate is determined by the thickness of the substrate, the angle of incidence of the airflow, and the airflow velocity.

In aspects according to the present disclosure, the catalyst on the surface of an air permeable substrate structure is a metal, a metal oxide, or mixtures thereof. Also provided for and included in the present disclosure are ceramic catalysts. Catalysts of the present disclosure include, but are not limited to, titanium dioxide, copper, copper oxide, zinc, zinc oxide, iron, iron oxide, or mixtures thereof. Suitable catalysts are provided, for example at Table 2. In some aspects, the catalyst is titanium dioxide in the form of anatase or rutile. In certain aspects, the titanium dioxide is the anatase form. In some aspects, the catalyst is titanium dioxide in the form of rutile. In other aspects, the titanium dioxide catalyst is a mixture of anatase and rutile. Anatase absorbs photons at wavelengths less than 380 nm, whereas rutile absorbs photons at wavelengths less than 405 nm. Also provided for, are catalysts on the surface that comprise tungsten trioxide ($WO_3$) that provides for the use of a full spectrum of light with energies of at least 2.85 eV. This extends the light source into the visible range of light beyond the range where $TiO_2$ is active alone. Not to be limited by theory, $WO_3$ provides new energy levels that $TiO_2$ does not support and allows for the adsorption of visible light with sufficient energy to oxidize water to hydroxyl radicals. Accordingly, the present disclosure further provides for and includes, sources of light that provide wavelengths in the visible range when paired with a suitable catalyst substrate.

TABLE 2

Photocatalysts having suitable Band-gap Energies

| Photocatalyst | Band-gap energy (electron volts (eV)) |
| --- | --- |
| Si | 1.1 |
| $WSe_2$ | 1.2 |
| CdS | 2.4 |
| $WO_3$ | 2.4-2.8 |
| $V_2O_5$ | 2.7 |
| SiC | 3.0 |
| $TiO_2$ (rutile) | 3.02 |
| $Fe_2O_3$ | 3.1 |
| $TiO_2$ anatase | 3.2 |
| ZnO | 3.2 |
| $SRTiO_3$ | 3.2 |
| $SnO_2$ | 3.5 |
| ZnS | 3.6 |

In certain aspects, the catalyst may be tungsten oxide or a mixture of tungsten oxide with another metal or metal oxide catalyst. In some aspects, the catalyst is selected from the group consisting of tungsten(III) oxide, tungsten(IV) oxide ($WO_2$), tungsten(VI) oxide ($WO_3$), and tungsten pentoxide. In an aspect, the tungsten oxide is tungsten dioxide ($WO_2$). In another aspect, the catalyst may be a tungsten trioxide ($WO_3$) catalyst combined with a cesium co-catalyst. (See "Development of a High-performance Photocatalyst that is Surface-treated with Cesium," available on the internet at www.aist.gojp/aist_e/latest_research/2010/20100517/20100517.html).

The catalysts of the present disclosure may further include one or more co-catalysts. In certain aspects, co-catalysts provide light absorbing capacity in the visible spectrum (e.g., wavelengths from about 390 nm to 700 nm). Suitable catalysts and methods to prepare catalysts to provide for catalysts suitable for devices having a light source that emits in the visible spectrum are known in the art. See, Tukenmez, "Tungsten Oxide Nanopowders and Its Photocatalytic Activity under Visible Light Irradiation," Thesis, Department of Molecular Biology, Umea University, Sweden, (2013) available on the internet at www.diva-portal.org/smash/get/diva2:643926/FULLTEXT01.pdf; Kim et al., "Photocatalytic Activity of $TiO_2$ Films Preserved under Different Conditions: The Gas-Phase Photocatalytic Degradation Reaction of Trichloroethylene," Journal of Catalysis 194(2): 484-486 (2000); Blake et al., "Application of the Photocatalytic Chemistry of Titanium Dioxide to Disinfection and the Killing of Cancer Cells," Separation and Purification Methods 28(1):1-50 (1999); Sugihara et al., "Development of a Visible Light Responsive Photocatalyst using Tungsten Oxide under Indoor Lighting," National Institute of Advanced Industrial Science and Technology (AIST) (2008). Co-catalysts of the present disclosure include, but are not limited to, platinum, gold. silver, copper, nickel, cesium, or palladium. In some aspects, the co-catalyst is a noble metal selected from the group consisting of gold, platinum, silver, rhodium, ruthenium, palladium, osmium, and iridium. In an aspect, the co-catalyst is gold. In another aspect, the co-catalyst is silver. In yet another aspect, the co-catalyst is platinum. In another aspect, the co-catalyst is an extruded ceramic. In certain aspects, the co-catalyst is zirconium dioxide ($ZrO_2$). In some aspects, the co-catalyst is an extruded titanium dioxide ceramic (see Shon et al., "Visible Light Responsive Titanium Dioxide ($TiO_2$)—a review" available at epress.lib.uts.edu.au).

The present disclosure also includes substrate catalysts comprising metallic palladium, copper and $WO_3$ that provide for photocatalytic reactions to take place up to 460 nm into the visible spectrum and provide a 7 fold increase in activity on the catalyst. In other aspects, the catalyst comprises a blend of $WO_3$ and $TiO_2$ that increases the photo catalytic reactions up to 60 fold at a wavelength of 410 nm. In a further aspect, the blend of $WO_3$ and $TiO_2$ provides for a light source comprising an XE lamp at 400 nm. In further aspects, the catalyst is spiked with nitrogen ions or $WO_3$ to provide for photocatalytic reactions in within the visible light spectrum. On other aspects, absorption in the visible spectrum is provided by photocatalysts comprising a blend of $TiO_2$ and $SiO_2$ to create a 3.3 eV gap.

TABLE 3

Co-catalysts and absorption wavelengths

| Co-catalyst | Wavelength |
| --- | --- |
| Gold (AU) | visible |
| Pt | |
| Ag | |
| titanium dioxide ceramic | visible |

Co-catalysts of the present disclosure may be provided in various amounts relative to the catalyst. In general, co-catalysts can be provided at levels of up to about 5%. In certain aspects, the amount of co-catalyst is 5% or less, though mixtures of co-catalysts having a combined amount of up to 10% may be used in certain aspects. In certain aspects, up to 1.0% of the total mass of the catalyst may be a co-catalyst of the types described above. In some aspects, the total amount of co-catalyst is up to 0.05%. In yet other aspects, the co-catalyst is provided at between 0.005 and 0.05%. In some aspects, the co-catalyst is provided at between 0.01 and 0.05%. In another aspect, the co-catalyst is provided at between 0.01% to 0.02%. In certain aspects, the co-catalyst is provided a less than 0.05% of the total mass of the catalyst.

The catalysts of the present disclosure may further include one or more additives. In an aspect, an additive may be a hygroscopic additive. Not to be limited by theory, it is thought that the presence of a hydroscopic additive increases the local concentration of water on the photocatalytic surface and thereby provide for non-hydrated purified hydrogen peroxide gas production at lower humidity levels and improves the efficiency of PGPG production at higher humidity levels. As provided herein, catalyst coatings having hygroscopic agents extend the efficiency of PHPG generating devices and extends the range of relative humidities wherein the PHPG generative device operates efficiently and can produce PHPG at a rate sufficient to establish a steady state concentration of PHPG of at least 0.005 ppm in a closed air volume of 10 cubic meters. In certain aspects, the relative humidity can be as low as 1%. In an aspect, the humidity of the ambient air is preferably above about 1% relative humidity (RH). In certain aspects the relative humidity can be from 1 to 99%. In other aspects, the humidity of the air flowing through the air permeable substrate is between 1% and 20% RH. In further aspects, the humidity of the air flowing through the air permeable substrate is at or above 5%. In other aspects, the humidity of the ambient air may be between about 10% and about 99% RH. In other aspects, the humidity of the ambient air may be between about 10% and about 99% RH. In certain aspects, the humidity of the air flow is less than 80%. In an aspect, the humidity is between 10% and 80%. In yet other aspects, the relative humidity is between 30% and 60%. In another aspect, the humidity is between 35% and 40%. In some aspects, the humidity of the air flowing through the air permeable substrate structure is between 56% and 59%.

In aspects according to the present disclosure, the hygroscopic additive may be selected from the group consisting of sodium bicarbonate, potassium bicarbonate, sodium carbonate, potassium carbonate, magnesium carbonate, magnesium bicarbonate, sodium hydroxide, potassium hydroxide, magnesium hydroxide, zinc chloride, calcium chloride, magnesium chloride, sodium phosphate, potassium phosphate, magnesium phosphate, carnallite ($KMgCl_3.6(H_2O)$), ferric ammonium citrate, nylon, acrylonitrile butadiene styrene (ABS), polycarbonate, cellulose, poly(methyl methacrylate), and combinations thereof.

In aspects according to the present disclosure, the hygroscopic additive may be a salt. In certain aspects, a hygroscopic additive may be a bicarbonate. In an aspect, the hygroscopic additive is sodium bicarbonate. In an aspect, the hygroscopic additive is potassium bicarbonate. In an aspect, the hygroscopic additive is magnesium bicarbonate. In other aspects, a hygroscopic additive may be a carbonate. In an aspect, the hygroscopic carbonate is sodium carbonate, potassium carbonate, or magnesium carbonate. In some aspects, the hygroscopic additive may be a hydroxide. In certain aspects, the hygroscopic additive may be sodium hydroxide, potassium hydroxide, or magnesium hydroxide. In some aspects, the hygroscopic additive may be a chloride. In certain aspects the hygroscopic additive may be zinc chloride, calcium chloride, or magnesium chloride. In yet other aspects, the hygroscopic additive may be a phosphate. In certain aspects, the hygroscopic phosphate may be sodium phosphate, potassium phosphate, or magnesium phosphate. It is understood that one or more hygroscopic compounds may be combined.

In general, additives can be provided at levels of up to about 5%. In certain aspects, the amount of additive is 5% or less, though mixtures of additives having a combined amount of up to 10% may be used in certain aspects. In certain aspects, up to 1.0% of the total mass of the catalyst may be an additives of the types described above. In some aspects, the total amount of additive is up to 0.05%. In yet other aspects, the additive is provided at between 0.005 and 0.05%. In some aspects, the additive is provided at between 0.01 and 0.05%. In another aspect, the additive is provided at between 0.01% to 0.02%. In certain aspects, the additive is provided at less than 0.05% of the total mass of the catalyst.

The present disclosure further provides for and includes a catalyst surface having a pH of 6.0 or greater. Not to be limited by theory, it is thought that the higher pH provides an improved source for oxidizable hydroxide ions during photocatalysis thereby increasing the production of non-hydrated purified hydrogen peroxide gas. In an aspect, the pH of the catalyst surface is greater than pH 7.0. In another aspect, the pH of the surface is between 7.0 and 9.0. In an aspect, the pH of the catalyst surface is between 7.0 and 8.5. In an aspect, the pH of the catalyst surface is between 7.0 and 8.0. In an aspect, the pH of the catalyst surface is between 7.0 and 7.5. In another aspect, the pH of the surface is between 7.5 and 9.0. In an aspect, the pH of the catalyst surface is between 7.5 and 8.5. In an aspect, the pH of the catalyst surface is between 7.5 and 8.0. In another aspect, the pH of the surface is between 8.0 and 9.0. In an aspect, the pH of the catalyst surface is between 8.0 and 8.5. In certain aspects, the pH of the surface is at least 7.5. In certain aspects, the pH of the surface is at least 8.0.

Catalysts of the present disclosure, optionally including co-catalysts and additives may be prepared according to methods known in the art. Suitable co-catalysis and additives include silver nitrate, cerium oxide and zinc oxide. Additives are included to reduce, for example, bacterial growth and to prevent UV induced degradation of the catalyst and air permeable substrate. The catalysts, co-catalysts and additives of the present disclosure may be applied to a mesh by a variety of methods including, but not limited to, gel sol methods, painting, dipping, and powder coating. In other aspects, the catalysts, co-catalysts and additives of the present disclosure may be applied to a mesh by toll coating, tape casting, ultrasonic spray, and web-based coating. As provided herein, the method of applying the catalysts, co-catalysts and additives is suitable if it provides for, and includes, retaining the mesh of the underlying air permeable substrate as recited above.

In an aspect, the catalyst mixture is applied to a mesh using a sol-gel method comprising the use of an alcoholic metal salt as the catalytic material. In certain aspects, the metal salt is $Ti(OR)_4$. Application of a catalyst mixture using the sol-gel method may further include organic and inorganic salts in the alcoholic solution to carry on hydration reaction, thereby producing organic metal compounds in gel form. The sol-gel methods may further include co-catalysts such as $WO_3$, $SnO_2$, $Fe_2O_3$, or $ZnO$. The gel solution may be applied by dipping the mesh into the gel solution or painting the solution onto the air-permeable substrate structure. The thickness of the catalyst mixture applied to the substrate may be controlled by controlling the dipping speed or by providing one or more coats. After drying, the coated substrate is baked and then sintered at high temperatures. In certain aspects, the catalytic mixture may further include noble metals or transition metals. In some aspects, the catalyst mixture may further include noble metals such as Au, Pd, Pt, or Ag, and some transition metals such as $MoO_3$, $Nb_2O_5$, $V_2O_5$, $CeO_2$, or $Cr_2O_3$.

The present disclosure provides for and includes devices having a source of light capable of illuminating the air permeable substrate structure having a catalyst on its surface. Not to be limited by theory, upon illumination, the catalyst absorbs photons of the appropriate wavelength and the energy is imparted to a valence band electron. The valence band electron is promoted to the conduction band creating an electron-hole or valence band hole. In the absence of an adsorbed chemical species, the promoted electron will decay and recombine with the valence band hole. Recombination is prevented when the valence band hole captures an electron from an oxidizable species—preferentially molecular water adsorbed to an active surface site on the photocatalyst. Concurrently, a reducible species adsorbed on the catalyst surface—preferentially molecular oxygen—may capture a conduction band electron.

Light sources suitable for devices of the present disclosure include both wide and narrow spectrum emission sources. In certain aspects, the light source may emit light in the ultraviolet (UV) spectrum. In other aspects, the light source may emit light in the visible spectrum. In yet other embodiments, the light source may emit light in both the visible and ultraviolet spectrums.

Suitable light sources according the present disclosure include, but are not limited to, lasers, light emitting diodes (LED), incandescent lamps, arc lamps, standard fluorescent lamps, U.V. lamps, and combinations thereof. In certain aspects, the light source is a light emitting diode.

The present disclosure provides for and includes illuminating an air-permeable substrate structure coated with a catalyst mixture using light of a suitable wavelength and intensity. As provided above, selection of a suitable illumination wavelength is determined by the catalyst and may be modified by the presence of one or more co-catalysts. In certain aspects, the light source provides ultraviolet light. In an aspect, the wavelength of the ultraviolet light is from 190 nm to 410 nm. In some aspects, where the light source may provide light having wavelengths of less than 190 nm, a suitable filter may be further provided to the device to block light at wavelengths of 190 nm and below. More specifically, certain devices of the present disclosure exclude light having a wavelength at or below 187 nm.

One of ordinary skill in the art would recognize that the production of ozone would result in the reduction of PHPG gas to water and oxygen:

$$O_3 + H_2O_2 \leftrightarrows H_2O + 2O_2$$

Accordingly, prior art designs that produce ozone are incompatible with the methods and devices of the present disclosure. As noted above, avoiding light at wavelengths below 190 nm for titanium dioxide containing catalysis greatly reduces or even eliminates ozone production and results in higher rates of PHPG production.

In certain aspects, the device includes an ultraviolet light source capable of illuminating a titanium dioxide containing catalyst mixture with light from 190 nm to 410 nm and may further include a filter to block light at wavelengths of 190 nm and below. In other aspects, the device includes both an ultraviolet light source providing illumination of a catalyst mixture containing titanium dioxide and further includes a co-catalyst that extends the absorption band of photocatalysis into the visible spectrum. In an aspect, the catalyst mixture may include tungsten trioxide, $WO_3$, that absorbs light in the visible spectrum. In an aspect, the light source may include light from 190 nm to 460 nm.

In further aspects, the light source provides ultraviolet light having a spectrum of light of 190 nm to 460 nm wherein 70% of the power is provided between 340 nm and 380 nm. In an aspect, at least 90% of the ultraviolet light is emitted between 340 nm and 380 nm. In another aspect, 99% of the ultraviolet light is emitted between 350 nm and 370 nm. In a further aspect, the ultraviolet light has a wavelength in the UVA range (315 nm to 400 nm). In some aspects, the light in the UVA range has a maximal intensity centered on or about 362 nm. In another aspect, the ultraviolet light has a wavelength in the UVA range and less than 1% in the UVB range (280 nm to 315 nm). In a further aspect, the ultraviolet light has a wavelength in the UVA range and less than 0.1% in the UVB range. In yet a further aspect, the ultraviolet light has a wavelength in the UVA range and less than 0.05% in the UVB range.

In aspects according to the present disclosure, a light source may have a power of 0.1 W to 150 W. In other aspects, the light source may be up to 150 W. In another aspect, the power may be at least 0.1 W. In an aspect, the light source has a power of at least 1 W. In a further aspect, the power may be greater than 2.5 W. In an aspect, the power may be about 5 W. In an aspect, the power may be 20 W. In certain aspects, the power of the light source may be up to 100 W. In certain aspects, the power is less than 100 W to minimize the destruction of PHPG produced. In other aspects, the power is between 1 W and 50 W. In certain aspects, the power of the light source is between 40 and 50 W.

Devices of the present disclosure include light sources providing an intensity of at least 0.1 watts per square inch (W/in$^2$) as measured at the air permeable substrate surface. In some aspects, the light source has an intensity of up to 150 W/in$^2$. In other aspects, the light source outputs light having an intensity of between 0.1 W/in$^2$ to 10 W/in$^2$. In an aspect, the intensity of the light illuminating the air permeable substrate is about 5 W/in$^2$. In certain aspects, the power at the substrate surface may be between 1 W/in$^2$ to 10 W/in$^2$. In another aspect, the intensity may be between 2 W/in$^2$ and 8 W/in$^2$. In an aspect, the intensity may be between 3 W/in$^2$ and 7 W/in$^2$. In yet another aspect, the power may be between 4 W/in$^2$ and 6 W/in$^2$.

Devices of the present disclosure are distinguishable from devices employing photocatalysis to produce reactive species that are designed for filtration. More specifically, devices of the present disclosure are degraded by the presence of contaminants such as dust, pollen, bacteria, spores, and particles that can occlude the open spaces of a mesh of the air permeable substrate. Similarly, volatile organic compounds (VOCs) which can react with reactive species, including hydrogen peroxide, decrease the production of PHPG and the distribution of PHPG to a space. Notably, while VOCs can be effectively reduced in a space by PHPG produced devices of the present disclosure, VOCs introduced into the device itself are preferably minimized or eliminated altogether. Accordingly, to maintain the efficiency of the devices and to maximize PHPG production, devices of the present disclosure may include one or more filters. As will be noted, the selection of the filters may be determined by the application and the type of space to be treated using PHPG. For example, a clean room in which air is already treated to eliminate dust, VOCs, and other contaminates could employ a device having an enclosure, an air distribution mechanism, a light source, and an air permeable substrate having a catalyst on its surface without requiring a prefilter. In contrast, a device for home use might require a dust filter and might further require a carbon filter to absorb VOCs. In certain aspects, the inclusion of an additional filter provides for the extended life of the air permeable catalyst coated substrates and provides for extended production of PHPG.

Filters used to purify air unrelated to PHPG generation are dependent on the air quality of the location in which the device is used. Inside an HVAC system with high quality air achieved by the filters of the HVAC system, no filters may be necessary before the air flow passes through the air permeable substrate of the PHPG device itself. The same holds true for stand-alone devices operating in areas where there is high air quality. When necessary, filters are generally selected from those known in the art that can achieve the filtration required with as little impedance of air flow necessary. Filters are further selected from those known in the art so that the filter itself does not also not introduce particulates or gasses into the airstream. Suitable filters that combine the functions of removing particulates as well as gaseous contaminants are known in the art. Filters require replacement regularly, with a frequency determined by the load placed upon the filter due to higher air quality (less frequent replacement) or lower air quality (more frequent replacement).

In most applications three filtration concerns are applicable. In certain applications, particulates or dust can foul the substrate matrix and the catalyst itself, so a particulate filter sufficient to the needs of the location may be used. In certain common aspects, a high air flow, pleated MERV 18 filter is employed. In other applications, volatile organic hydrocarbons may require filtration and this may be accomplished using a number of different activated charcoal or carbon impregnated filters that are known in the art. In yet other applications, certain inorganic gasses such as nitrogen oxides need to be removed by filtration. To remove nitrogen oxides, a zeolite filter is usually employed. In some aspects, the PHPG device includes impregnated zeolite filters that are capable of removing volatile organic hydrocarbons and nitrogen oxides in a single, combined material and stage. Suitable filters are known in the art that can remove particles of various sizes that would otherwise block the air permeable substrate or contaminate and inactivate the catalytic surface.

In aspects of the present disclosure, devices may further include one or more filters designed to remove contaminants selected from nitrogen oxides (NOx), sulfur oxides (SOx), volatile organic compounds, dust, bacteria, pollen, spores, and particles. In certain aspects, the device includes one or more filters selected from an organic vapor filter, a particulate filter, a high efficiency filter, a hydrophobic filter, an activated charcoal filter, or a combination thereof.

In certain aspects, pre-filters remove volatile organic compounds, NOx, and SOx. In some aspects, the filters remove aldehydes such as formaldehyde or acetaldehyde. In other aspects, the filters remove VOCs including toluene, propanol, and butene. In yet other aspects, pre-filters remove the mono-nitrogen oxides NO and $NO_2$ (e.g., NOx). In other aspects, pre-filters remove sulfur and oxygen containing compounds known as SOx. SOx compounds removed by filters of the present disclosure include SO, $SO_2$, $SO_3$, $S_7O_2$, $S_6O_2$, $S_2O_2$, or combinations thereof. Prefilters of the present disclosure may be employed to remove any combination of VOCs, NOx, and SOx.

In certain aspects, the devices include a filter comprising a microporous aluminosilicate mineral. In an aspect, a filter of the present device may be a zeolite filter. In an aspect, the zeolite may be analcime, chabazite, clinoptilolite, heulandite, natrolite, phillipsite, or stilbite. In certain aspects, the zeolite may be a synthetic zeolite. In an aspect, the device includes a zeolite filter for the removal of NOx, SOx, or both. Suitable filters are known in the art.

In other aspects, the devices include a filter comprising a particulate filter. In certain aspects, the particulate filter is a 3 m ultra allergan filter. A suitable example of a particle filter can be obtained from Air Filters, Inc, which provides Astro-cell mini-pleat filters. One of ordinary skill in the art would be able to select filters that provide suitable air flow levels and resistance to air flow to provide for a sufficient air flow through the air permeable substrate as recited above.

In yet other aspects, suitable filters for devices of the present disclosure include carbon filters, charcoal filters, or activated carbon filters. In some aspects, the filter is a GAC (granular activated carbon) carbon filter. In an aspect, the GAC is a filter prepared from coconut shells. In an aspect, the filter is a powdered activated carbon (R 1) (PAC). In another aspect, the filter is an extruded activated carbon (EAC) filter. In an aspect, the filter may be a bead activated carbon (BAC) filter. In an aspect, the filter may be an impregnated carbon filter. In certain aspects, an impregnated carbon filter is included in a device to remove hydrogen sulfides (H₂S) and thiols. Suitable impregnated carbon filters are known in the art.

Air filtration in devices according to the present disclosure provide for air flows across the air permeable substrate layer having low levels of contaminants and photocatalysis inhibitors.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following Examples. The following Examples are presented for the purposes of illustration and should not be construed as limitations.

EXAMPLES

Example 1: Measurements of PHPG, Ozone, VOC's, Temperature, and Humidity

All PHPG concentration readings take place with Draeger products. A Pac III, Polytron 7000 or Draeger Tube is utilized in all tests, generally according to manufacturer's instructions. The Polytron displays a digital reading when air is drawn through the mesh sensor. Most commonly, Draeger Tubes are used after clipping on both ends and placement in a ACCURO™ Pump. Per manufacturer instructions, the tubes are pumped 100 times and the level of PHPG determined by observing the color change in the crystals. The PAC III has proved to be generally less effective in measuring very low levels of PHPG.

Measurements for ozone, VOC's, temperature, and humidity were all accomplished using standard devices. Draeger tubes, designed to detect hydrogen peroxide concentrations as low as 0.10 ppm after drawing 2000 cubic centimeters of air, are found to provide readings of lower concentrations accurate within 0.005 ppm, as larger volumes are drawn by a calibrated pump—for example, a Draeger tube that indicated 0.10 ppm after drawing 4000 cubic centimeters measure an approximate PHPG concentration of 0.05 ppm, and a Draeger tube that indicated 0.10 ppm after drawing 6000 cubic centimeters, measured an approximate PHPG concentration of 0.033 ppm.

Example 2: PHPG Devices Testing Air Permeable Substrates

Figure 2A:
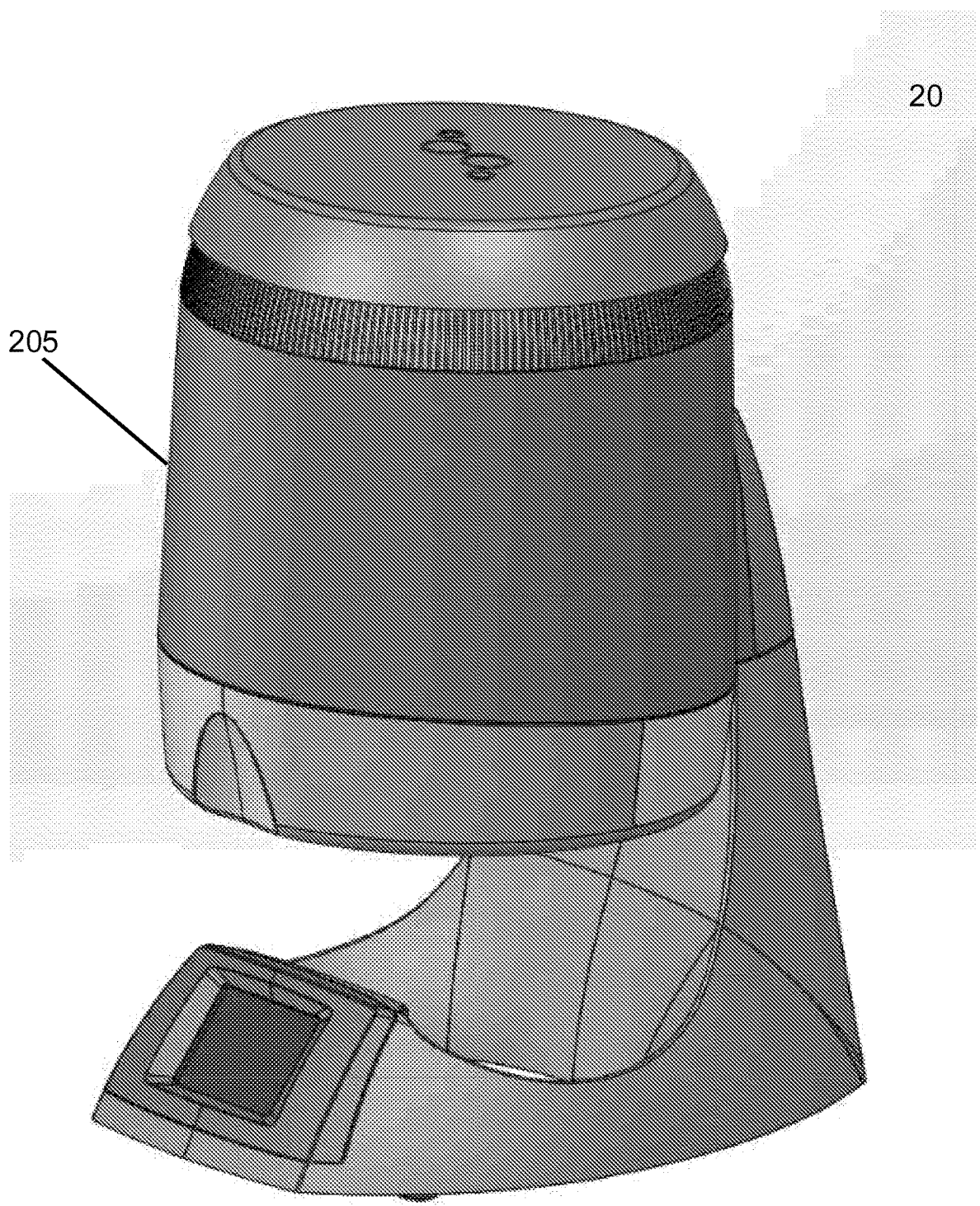
FIGS. 2A to 2C are illustrations of an exemplary stand alone PHPG generating device according the present disclosure.
Figure 2B:
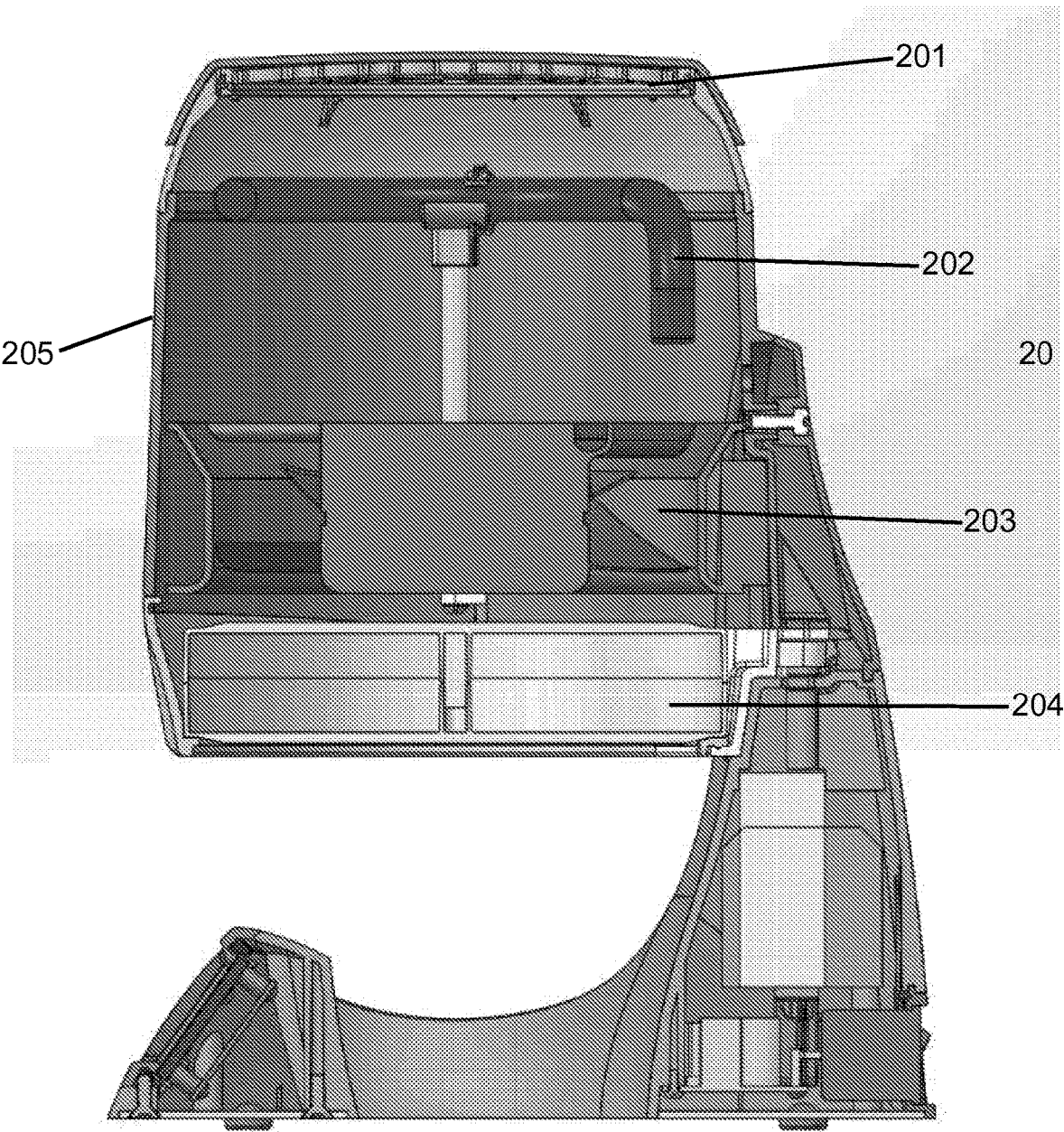
Figure 2C:
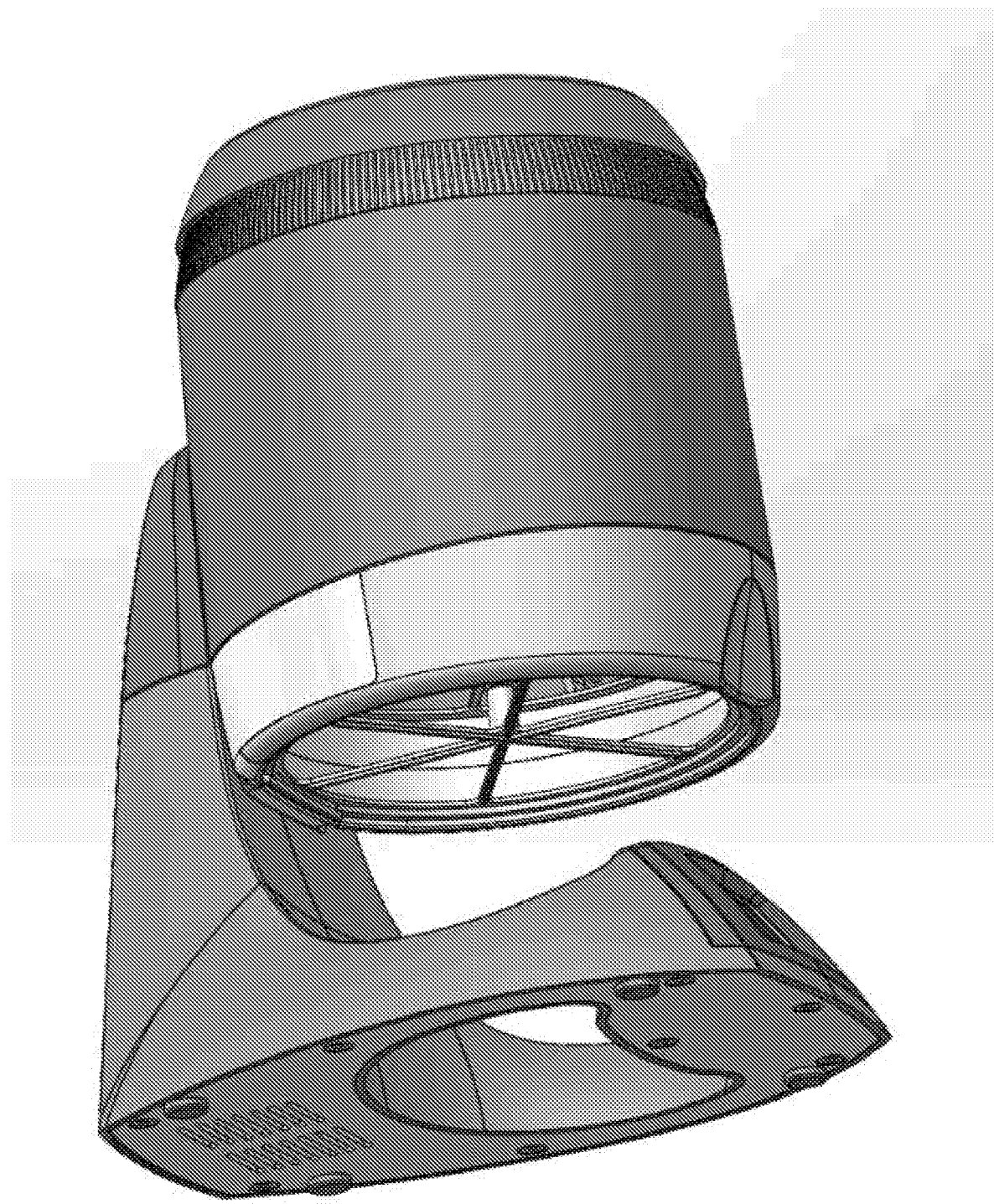

A PHPG generating device 20 as illustrated in FIGS. 2A to 2B comprising an enclosure 205, an air permeable substrate 201, an air distribution mechanism 203 and a light source 203 is used for testing. The air permeable substrates 201 are prepared by dip coating a polyester mesh in a 10 to 35% slurry of the anatase form TiO₂ in water and allowed to air dry. To prevent clogging of the open holes of the mesh, air is blown through the air permeable substrate. The air distribution mechanism is set on its highest setting and provides an airflow of about 115 cubic feet per minute. The humidity of the room is maintained at approximately 55%. The PHPG generating device is allowed to operate in a 140 square foot closed room with 8 foot ceilings for 1 hour and then the steady state level of PHPG is determined. Absent the continued operation of the PHPG generating device, the PHPG dissipates and is undetectable within about 5 minutes. Ozone is not detected in any of the tests.

Example 3: Effect of Mesh Variation on PHPG Production

The effects of mesh variation on PHPG production is performed by replacing the TiO₂ coated air permeable substrate 201 as provided in Table 4 and testing as described in Example 2.

TABLE 4

Comparison of Air Permeable Substrates

| Thread Thickness (inches) | Hole Size (inches) | Strands Per Inch | Thread Thickness (μm) | Hole size (μm) | Strands per cm | Open Area % | PHPG (ppm) |
|---|---|---|---|---|---|---|---|
| 0.0019 | 0.001 | 460 | 48 | 25 | 181 | 21 | 0.1 |
| 0.0024 | 0.002 | 280 | 61 | 51 | 110 | 30 | 0.4 |
| 0.0045 | 0.004 | 140 | 114 | 102 | 55 | 37 | 0.3 |
| 0.0051 | 0.006 | 109 | 130 | 152 | 43 | 45 | 0.3 |
| 0.006 | 0.008 | 80 | 152 | 203 | 31 | 41 | 0.6 |
| 0.013 | 0.012 | 50 | 330 | 305 | 20 | 37 | n/d |
| 0.016 | 0.032 | 24 | 406 | 813 | 9 | 58 | n/d | n/d = not detected

Example 4: Effect of Angle of Incidence on PHPG Production

The device according to Example 2 is modified by attaching a 10 inch aluminum adaptor as a shroud to the top of the device that allows for rotation of the air permeable substrate 201. An air permeable substrate having 152 micron threads and an open area of 41% is placed in the device. The initial steady state level of PHPG, measured having the airflow at 90°, is 0.7 ppm. The air permeable substrate 201 is rotated within the shroud in 2° increments and the steady state level of PHPG measured until the polytron no longer detects hydrogen peroxide. Production of PHPG is maintained from about 90° to about 68° (e.g., 22° off perpendicular). Beginning at about 68°, PHPG levels decreases steadily from 68° degrees to about 14° at approximately 0.1 ppm per 10°. No PHPG production is detected when the incident angle of the airflow was below 14°.

Although the invention has been described in conjunction with specific embodiments thereof, it is evident that many alternatives, modifications and variations will be apparent to those skilled in the art. Accordingly, it is intended to embrace all such alternatives, modifications, and variations that fall within the spirit and broad scope of the appended claims.

All publications, patents, and patent applications mentioned in this specification are herein incorporated in their entirety by reference into the specification, to the same extent as if each individual publication, patent, or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

The invention claimed is:

1. A device for producing non-hydrated purified hydrogen peroxide gas (PHPG) comprising:
   a. an enclosure;
   b. an air distribution mechanism providing an airflow;
   c. an air-permeable substrate structure that is a mesh having a percentage of open area between 10% and 60%, said mesh having a catalyst on its surface;
   d. a source of light; and
   wherein said airflow is through said air-permeable substrate structure; and
   said device produces PHPG and directs it out of said enclosure when in operation.

2. The device of claim 1, wherein said catalyst comprises titanium dioxide and said source of light is a source of ultraviolet light.

3. The device of claim 1, wherein said catalyst comprises tungsten trioxide or a mixture of titanium dioxide and tungsten trioxide and said source of light is visible light with an energy of at least 2.85 electron volts (eV).

4. The device of claim 1, wherein said catalyst comprises titanium dioxide.

5. The device of claim 1, wherein said catalyst comprises tungsten trioxide or a mixture of titanium dioxide and tungsten trioxide.

6. The device of claim 1, wherein the thickness of said catalyst on the surface of said air permeable substrate structure is between 250 nm and 750 nm thick.

7. A device for producing non-hydrated purified hydrogen peroxide gas (PHPG) when installed into a heating, ventilating, and air conditioning (HVAC) system comprising:
   a. an air-permeable substrate structure that is a mesh having a percentage of open area between 10% and 60%, said mesh having a catalyst on its surface; and
   b. a source of light;
   wherein air flows from the HVAC system through said air-permeable substrate structure and said device produces PHPG and directs it away from said air-permeable substrate structure having a catalyst on its surface when in operation and into a heated, ventilated and air conditioned space.

8. The device of claim 7, wherein said catalyst comprises titanium dioxide and said source of light is a source of ultraviolet light.

9. The device of claim 7, wherein said catalyst comprises tungsten trioxide or a mixture of titanium dioxide and tungsten trioxide and said source of light is visible light with an energy of at least 2.85 eV.

10. The device of claim 7, wherein said HVAC system further comprises one or more filters to remove one or more contaminants from said airflow prior to flowing through said air-permeable substrate structure selected from the group consisting of nitrogen oxide (NOx), sulfur oxide (SOx), volatile organic molecules (VOM), household dust, pollen, dust-mite debris, mold spores, pet dander, smoke, smog, and bacteria.

11. The device of claim 7, wherein the thickness of said catalyst on its surface that is between 5 nm and 750 nm thick.

* * * * *